United States Patent
Kato

(10) Patent No.: US 9,247,894 B2
(45) Date of Patent: Feb. 2, 2016

(54) APPARATUS AND METHOD FOR WHITE-MATTER-ENHANCEMENT PROCESSING

(76) Inventor: Toshinori Kato, Tokyo (JP)

(*) Notice: Subject to any disclaimer, the term of this patent is extended or adjusted under 35 U.S.C. 154(b) by 381 days.

(21) Appl. No.: 12/647,208

(22) Filed: Dec. 24, 2009

(65) Prior Publication Data

US 2011/0004092 A1 Jan. 6, 2011

Related U.S. Application Data

(63) Continuation of application No. PCT/JP2008/061762, filed on Jun. 27, 2008.

(30) Foreign Application Priority Data

Jun. 29, 2007 (JP) .................................. 2007-173550

(51) Int. Cl.
*A61B 5/00* (2006.01)
*A61B 5/055* (2006.01)
(Continued)

(52) U.S. Cl.
CPC .................. *A61B 5/055* (2013.01); *A61B 5/107* (2013.01); *G01R 33/5608* (2013.01);
(Continued)

(58) Field of Classification Search
CPC .. A61B 5/055; A61B 5/107; A61B 2576/026; G01R 33/5608; G01R 33/5602
USPC .......... 600/407, 408, 410–423; 324/306–309, 324/318–322
See application file for complete search history.

(56) References Cited

U.S. PATENT DOCUMENTS 6,751,495 B2 * 6/2004 Maier et al. ................... 600/410
7,145,336 B2 * 12/2006 Brown .......................... 324/309
(Continued)

FOREIGN PATENT DOCUMENTS

JP 9-253067 A 9/1997
JP 2001-070285 A 3/2001
(Continued)

OTHER PUBLICATIONS

O Ciccarelli, AT Toosy, GJM Parker, CAM Wheeler-Kingshott, GJ Barker, DH Miller, AJ Thompson. "Diffusion tractography based grouped mapping of major white-matter pathways in the human brain." NeuroImage 19(2003), pp. 1545-1555.*
(Continued)

*Primary Examiner* — Amanda Lauritzen Moher
(74) *Attorney, Agent, or Firm* — Amin, Turocy & Watson, LLP

(57) ABSTRACT

The present invention provides an apparatus for white-matter-enhancement processing, and a method and a program for white-matter-enhancement processing that makes it possible to analyze distinguishing characteristics of the brain of a living body, such as degree of growth and development, left/right brain dominance, areas of strength and weakness, and personality traits. The apparatus for white-matter-enhancement processing of the present invention has a memory part for inputting and storing contrast images of a brain of a living body; a white-matter-enhanced image-creating part for creating white-matter-enhanced images, based on stored contrast images; a display processing part for displaying the white-matter-enhanced images thus created; and a branching analysis part for analyzing distinguishing characteristics of the brain of a living body, based on any one of or a combination of the characteristics of branches in the white-matter-enhanced images that are created: their number, thickness, length, location, intensity, shape and/or size.

14 Claims, 31 Drawing Sheets

(51) Int. Cl.
*A61B 5/107* (2006.01)
*G01R 33/56* (2006.01)
*G06T 5/00* (2006.01)

(52) U.S. Cl.
CPC .......... *G06T 5/007* (2013.01); *A61B 2576/026* (2013.01); *G01R 33/5602* (2013.01); *G06T 2207/10088* (2013.01); *G06T 2207/30016* (2013.01)

(56) References Cited

U.S. PATENT DOCUMENTS

| | | | | |
|---|---|---|---|---|
| 7,671,592 | B2* | 3/2010 | Kabasawa | 324/309 |
| 8,600,135 | B2* | 12/2013 | Patriarche et al. | 382/131 |
| 2001/0039377 | A1* | 11/2001 | Maier et al. | 600/410 |
| 2004/0170308 | A1* | 9/2004 | Belykh et al. | 382/128 |
| 2005/0283053 | A1* | 12/2005 | deCharms | 600/300 |
| 2006/0270926 | A1* | 11/2006 | Hu et al. | 600/407 |
| 2007/0167788 | A1* | 7/2007 | Hartlep et al. | 600/447 |
| 2009/0252391 | A1 | 10/2009 | Matsuda et al. | |
| 2010/0174171 | A1* | 7/2010 | Lee et al. | 600/410 |
| 2011/0301495 | A1* | 12/2011 | Hirsch | 600/559 |

FOREIGN PATENT DOCUMENTS

| | | |
|---|---|---|
| JP | 2002-209867 A | 7/2002 |
| WO | WO2007/023522 A1 | 3/2007 |
| WO | WO2008007801 A1 | 1/2008 |

OTHER PUBLICATIONS

O Ciccarelli, GJM Parker, AT Toosy, CAM Wheeler-Kingshott, GJ Barker, PA Boulby, DH Miller, AJ Thompson. "From diffusion tractography to quantitative white matter tract measures: a reproducibility study." NeuroImage 18(2003), pp. 348-359.*

* cited by examiner (A)

Thalamus: Brain address T (B)

Basal ganglia of the cerebrum:
Brain address G (C)

9 Corpus callosum

Left brain   Right brain (B)

(A)

(A)

(B)

(A)

(B)

(C)

APPARATUS AND METHOD FOR WHITE-MATTER-ENHANCEMENT PROCESSING

This is a continuation application of International Application no. PCT/JP08/061762 filed Jun. 27, 2008 and published in Japanese, which has a priority of Japanese Application no. JP 2007-173550 filed Jun. 29, 2007, both hereby incorporated by reference.

TECHNICAL FIELD

The present invention relates to an apparatus for white-matter-enhancement processing, and a method and a program for white-matter-enhancement processing; it particularly concerns an apparatus for white-matter-enhancement processing and a method and program for white-matter-enhancement processing that utilize contrast images of the brain of a living body obtained by means of a magnetic resonance imaging (MRI) apparatus.

BACKGROUND ART

CT (computed tomography scanning) apparatus, MRI apparatus and the like are generally known as apparatus for imaging the shape of the brain.

A CT apparatus is an apparatus that uses the method of computed tomographic imaging: a device for outputting x-ray radiation rotates around a living body and irradiates it from multiple directions, and a computer performs calculations on the detected data to create images.

An MRI apparatus is an apparatus that uses the method of magnetic resonance imaging: the spin of atomic nuclei of the body tissue of a subject placed in a static magnetic field is excited by high wavelength signals for the particular Larmor frequency for those nuclei, and images are created from magnetic resonance signals that are given off accompanying this excitation.

Each of these apparatus—CT and MRI—has been developed with the goal of detecting brain structure, brain lesions, and the like.

Because the CT apparatus can clearly distinguish between the skull and the brain matter, it is used for preoperative examination before brain surgery. It is also capable of rendering blood vessels as small as 1 mm.

However, because of the exposure to radiation accompanying the CT apparatus use, with rare exceptions, CT is not performed on healthy persons as a rule, and it is only selected as a last option and used when there is a suspicion of illness. For example, a CT scan of the lungs might be performed in a regularly scheduled physical examination, but this would be to find a small tumor in the lungs, or the like. In this way, the use of CT apparatus is restricted in brain structural imaging because of radiation exposure. In addition, although images can be obtained distinguishing the cortex and the white matter of the brain, they have not been as clear as could be desired.

With the MRI apparatus, on the other hand, there are no constraints on its use in brain structural imaging because there is no fear of radiation exposure, and images can be obtained as easily and freely as photographs of the brain. Currently, because it can even detect brain lesions of around 1 mm, it is used even in regularly scheduled physical examinations. Three-dimensional (3D) MRI is also commonly used, and it has become possible to investigate the structure of the brain in detail by reconstructing it from any angle.

In addition, the MRI apparatus does an excellent job of visualizing the brain structure at the corticomedullary junction, which divides the cortex and the white matter.

Five types of imaging methods are normally used in brain MRI: T1-weighted imaging, proton-weighted imaging, T2-weighted imaging, FLAIR imaging and diffusion-weighted imaging.

In T1-weighted images, the white matter is rendered in white, and the cortex, in gray. Lesions are mainly rendered in shades of black.

In proton-weighted images, T2-weighted images and FLAIR (Fluid Attenuated Inversion Recovery) images, the white matter is, conversely, rendered in black, and the cortex, in gray. Lesions are mainly rendered in white.

In diffusion-weighted images, the cortex and white matter are rendered uniformly in gray, and lesions are rendered in white. As an example of technology concerning conventional MRI apparatus, Patent Reference 1 proposes a magnetic resonance imaging method and apparatus in which, in a magnetic resonance imaging method wherein a subject body placed in a static magnetic field is subjected first to an inversion sequence including inversion pulses, and after the inversion sequence, to an imaging sequence for collecting magnetic resonance signals from the subject body, the frequency band width of the inversion pulses is set wider than previously used bandwidths.

This magnetic resonance imaging method and apparatus makes it possible, in magnetic resonance imaging using an IR series sequence including inversion pulses, to perform imaging that actively utilizes the phenomena of chemical exchange and/or cross relaxation among a pool of a plurality of kinds of atomic nuclei; and it is stated, for example, that contrast is improved between white matter and gray matter and the like, and that the S/N ratio is improved, thus improving, for example, its ability to render brain neural tissue, and making it possible to obtain MRI images of previously unobtainable high quality. (This technology will be referred to below as Previous Example 1.)

In addition, Patent Reference 2 proposes a magnetic resonance imaging apparatus in which, in a magnetic resonance imaging apparatus provided with an acquisition means, whereby a nuclear magnetic resonance signal is generated at the subject body under specified conditions of image acquisition and then detected, a reconstruction means for reconstructing tomographic images of the subject body based on nuclear magnetic resonance signals, a display means for displaying tomographic images of the subject body, and a control means for controlling the image acquisition means, the reconstruction means and the display means; the control means continuously displays at least 2 types of contrast images on the same screen or on a plurality of screens. For the plurality of types of contrast images, 2 types of contrast images, such as a proton density-weighted image and a T2-weighted image, a T1-weighted image and a T2-weighted image, or a fat-water synthetic image and a fat-suppressed image can be selected according to the lesion being targeted.

This magnetic resonance imaging apparatus is said to make it possible to advance a puncture needle, biopsy needle or the like to a lesion site in a subject body with an image corresponding to the lesion and rendered with higher contrast as a guide. (This technology will be referred to below as Previous Example 2.)

Patent Reference 1: Tokkai [Japan unexamined patent application publication] no. H9-253067
Patent Reference 2: Tokkai no. 2001-70285

Problem to be Solved by the Invention

Both Previous Example 1 and Previous Example 2 were technologies for the purpose of improving the rendering of contrast images in order to specify the range, size, location and the like of a lesion; they were not technologies for the purpose of analyzing distinguishing characteristics of the brain of a living body, such as degree of growth and development, left/right brain dominance, identification of areas of strength and weakness, and personality traits of the brain of the living body.

It is an object of the present invention to provide an apparatus for white-matter-enhancement processing and a method and a program for white-matter-enhancement processing that make it possible, by creating white-matter-enhanced images in which the brain white matter is enhanced from contrast images of the brain of a living body obtained from an MRI apparatus, to analyze distinguishing characteristics of the brain of a living body, such as degree of growth and development, left/right brain dominance, identification of areas of strength and weakness, and personality traits of the brain of the living body.

Means for Resolution of the Problem

The apparatus for white-matter-enhancement processing of the present invention comprises means for creating a white-matter-enhanced image for enhancing white matter, based on a contrast image of the brain of a living body obtained by means of an MRI apparatus, in which the white matter is enhanced by adjusting the contrast image in such a way that the white matter stands out and the cortex does not stand out, and means for displaying the white-matter-enhanced image that was created.

The contrast image is, for example, a T1-weighted image, a proton density-weighted image, a T2-weighted image, a FLAIR image or a diffusion-weighted image, or an image that is a combination thereof.

The white-matter-enhanced image may be created by adjusting the window width and window level.

"Addresses" for demarcating regions of the brain, which are assigned demarcating sites where specified functions and roles are performed in the brain of the living body, may also be displayed together with the white-matter-enhanced image.

The invention may have a means for analyzing distinguishing characteristics of a brain of a living body, based on the number, thickness, length, location, intensity, shape or size, or a combination of these characteristics, of the branches in the white-matter-enhanced image that was created.

The analysis means may create and analyze a plurality of types of classifications based on characteristics of the white-matter-enhanced images of brains of living bodies.

The method for white-matter-enhancement processing of the present invention comprises the steps of:

inputting a contrast image of a brain of a living body obtained by means of an MRI apparatus;

creating a white-matter-enhanced image, based on the contrast image that was input, in which the white matter is enhanced by adjusting the contrast image in such a way that the white matter stands out and the cortex does not stand out; and displaying the white-matter-enhanced image that was created.

The analysis step may create and analyze a plurality of types of classifications based on characteristics of the white-matter-enhanced images of living bodies.

The program of the present invention makes the computer execute the processes of:

inputting a contrast image of the brain of a living body obtained by means of an MRI apparatus;

creating a white-matter-enhanced image, based on the contrast image of the brain of a living body that was input, in which the white matter is enhanced by adjusting this contrast image in such a way that the white matter stands out and the cortex does not stand out; and displaying the white-matter-enhanced image that was created.

The program of the present invention makes the computer execute a process for analyzing distinguishing characteristics of the brain of a living body, based on the number, thickness, length, location, intensity, shape or size, or a combination of these characteristics, of the branches in the white-matter-enhanced image that was created.

The analysis process may create and analyze a plurality of types of classifications based on characteristics of the white-matter-enhanced images of brains of living bodies.

Effect of the Invention

The present invention, by creating white-matter-enhanced images in which the brain white matter is enhanced from contrast images of the brain of a living body obtained from an MRI apparatus, makes it possible to analyze distinguishing characteristics of the brain of a living body, such as degree of growth and development of the brain of the living body, left/right brain dominance, identification of areas of strength and weakness, and personality traits of the living body.

Figure 1:
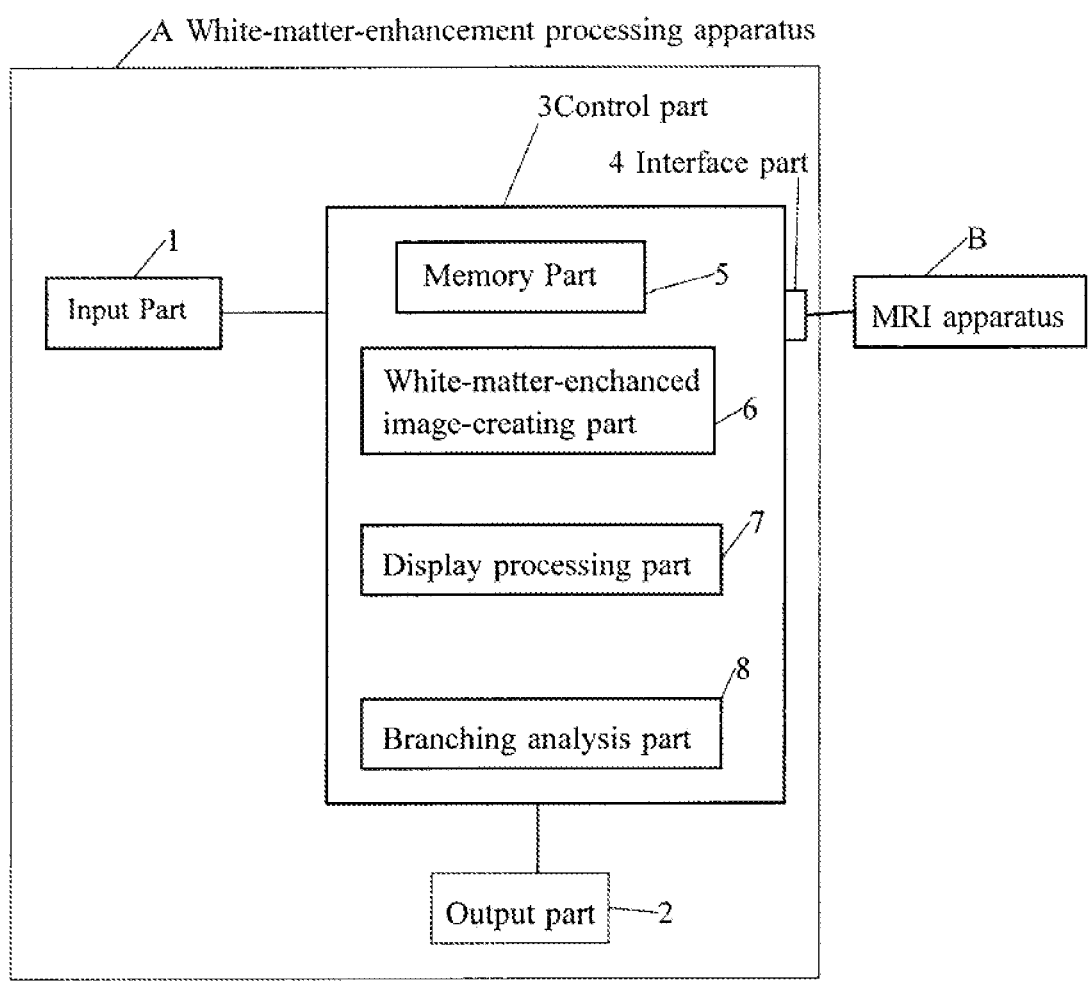
FIG. 1 is a block diagram showing the constitution of a white-matter-enhancement processing apparatus of an example of an embodiment of the present invention.

A: Apparatus for white-matter-enhancement processing
B: MRI apparatus
C: Input part
D: Output part (display part)
3: Control part
4: Interface part
5: Memory part
6: White-matter-enhanced image-creating part
7: display processing part
8: branching analysis part

BEST MODE FOR CARRYING OUT THE INVENTION

An embodiment of the present invention is explained below, with reference to the figures.

Constitution of the Apparatus for White-Matter-Enhancement Processing

FIG. 1 is a block diagram showing the constitution of a white-matter-enhancement processing apparatus of an example of an embodiment of the present invention.

As shown in FIG. 1, white-matter-enhancement processing apparatus A of an example of an embodiment of the present invention has an input part 1 constituting a keyboard, a mouse and the like for inputting various data, an output part (display part) 2 constituting a display and the like, and a control part 3, which controls input part 1 and display part 2; and it is connected to MRI apparatus B through an interface part 4.

Control part 3 has a memory part 5 for inputting and storing contrast images of the brain of a living body, obtained by means of MRI apparatus B; a white-matter-enhanced image-creating part 6 for creating white-matter-enhanced images based on contrast images stored in recording part 5, in which the white matter is enhanced by adjusting the images in such a way that the white matter stands out and the cortex does not stand out; a display processing part 7 for displaying on output part 2 the white-matter-enhanced images created by means of white-matter-enhanced image-creating part 6; and a branching analysis part 8 for analyzing distinguishing characteristics of the brain of the living body, based on any one of or a combination of the characteristics of branches in the white-matter-enhanced images that are created: their number, thickness, length, location, intensity, shape and/or size.

Contrast images input from MRI apparatus B can be any of T1-weighted images, proton-weighted images, T2-weighted images or diffusion-weighted images, or a combination thereof.

Operation of the White-Matter-Enhancement Processing Apparatus

Figure 2:
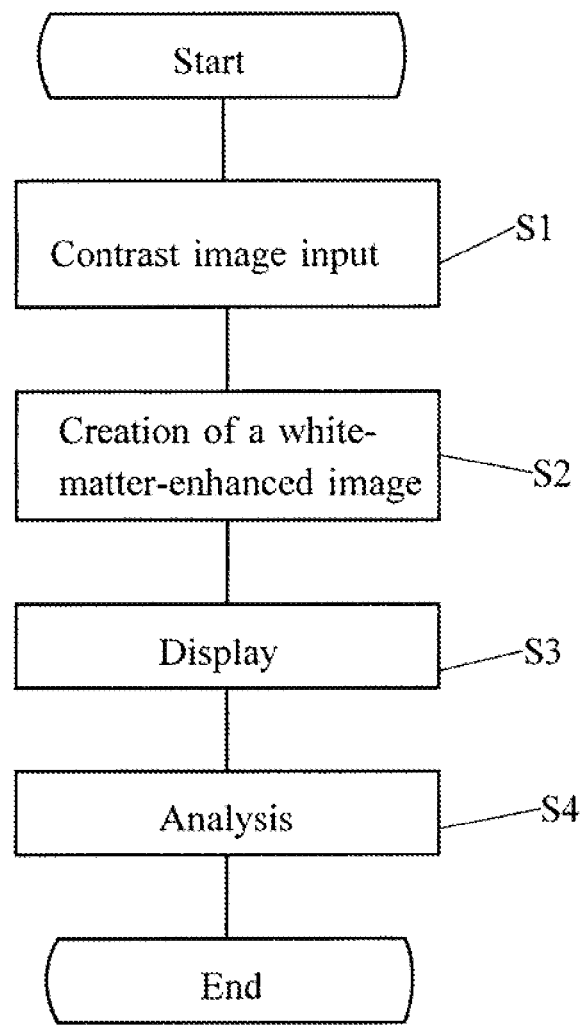
FIG. 2 is a flow chart for explaining the operation of a white-matter-enhancement processing apparatus of an example of an embodiment of the present invention.

FIG. 2 is a flow chart for explaining the operation of a white-matter-enhancement processing apparatus of an example of an embodiment of the present invention.

First, a contrast image of the brain of a living body obtained by means of MRI apparatus B is input (Step S1). In obtaining the images from MRI apparatus B, the imaging parameters repetition time (TR) and echo time (TE) are adjusted to enhance the contrast between the cortex and the white matter. For example, TR is set at around 4000 ms, and TE, at 20-200 ms.

For a left/right comparison from a single image, a horizontal cross-section, or a coronal cross-section, is preferable to a sagittal cross-section.

Next, a white-matter-enhanced image is created based on the input contrast image, in which the white matter is enhanced by adjusting the image in such a way that the white matter stands out and the cortex does not stand out (Step S2).

Figure 3:
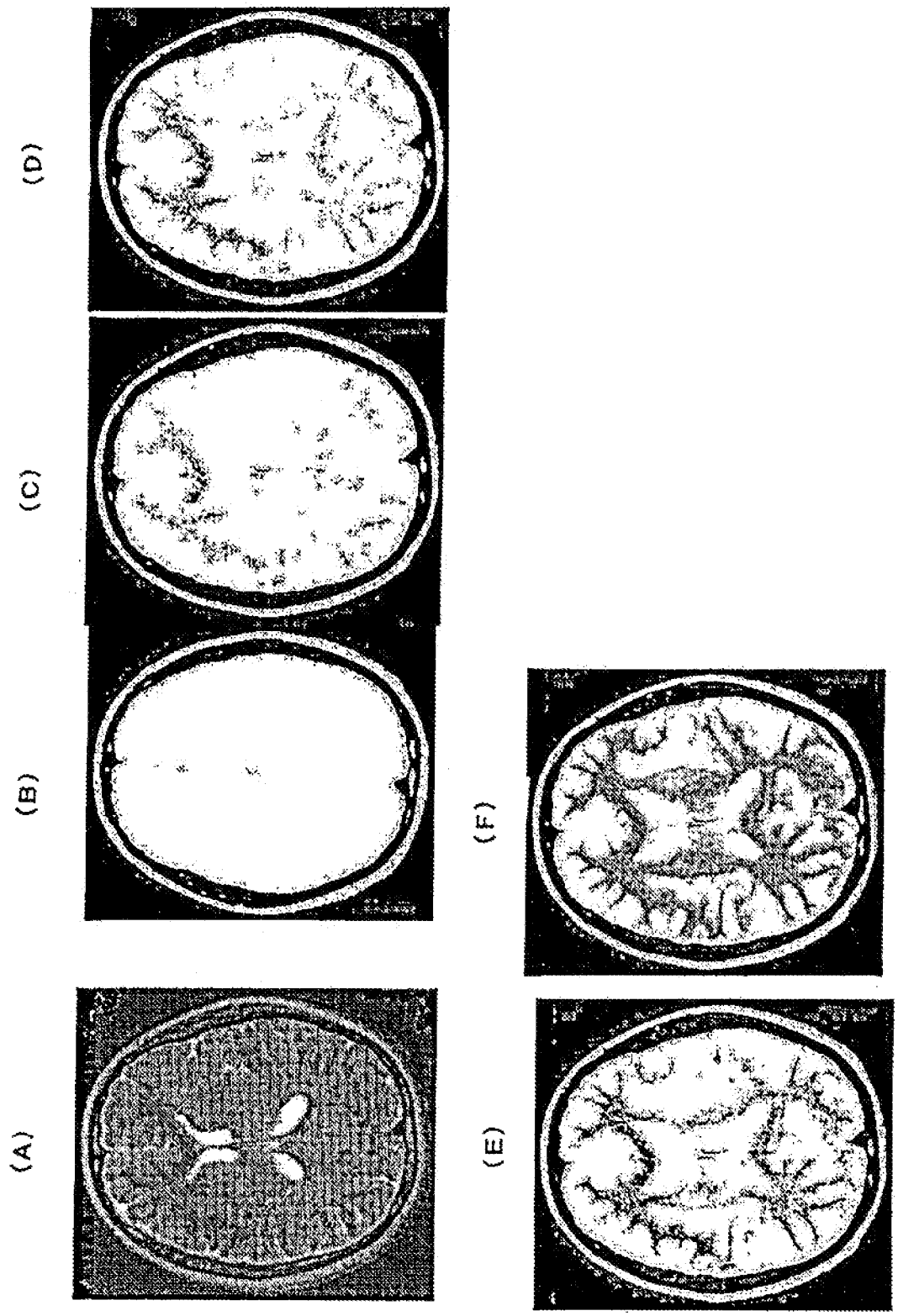
FIG. 3(A)-(F) are explanatory views for explaining the process of creating a white-matter-enhanced image.

In FIG. 3, (A)-(F) are explanatory views for explaining the process of creating a white-matter-enhanced image. In white-matter-enhanced image-creating part 6, a white-matter-enhanced image is created by the operation of input part 1 by an operator to adjust the window width and window level. For example, if the contrast image is a T2-weighted image (FIG. 3(A)), the window width is set to zero or around zero to make the cortex white (FIG. 3(B)) and the window level is gradually increased from zero to 200-300 to make all the white matter black (FIG. 3, (B)-(E)), and a white-matter-enhanced image (FIG. 3(F)) is thus obtained.

It can be seen that, in a white-matter-enhanced image, changing and thus enhancing the contrast of the interior of the white matter causes the frontal lobe white matter to be rendered blacker than the temporal lobe or occipital lobe white matter. This fact suggests that the bundles of white matter fiber such as myelin are thicker and denser. It has also been shown that the internal structure of the white matter can be distinguished not only in the period when myelination first occurs, from the neonate until around 2 years of age, but even after 3 years of age and after becoming an adult.

The white-matter-enhanced image created is subsequently displayed by means of output part 2 (Step S3). At that time, addresses for demarcating regions of the brain, which are assigned demarcating sites where specified functions and roles are performed in the brain of a living body (called "brain addresses" in Japanese, nou banchi: registered trademark by the inventor), may also be displayed together with the white-matter-enhanced image.

Figure 4:
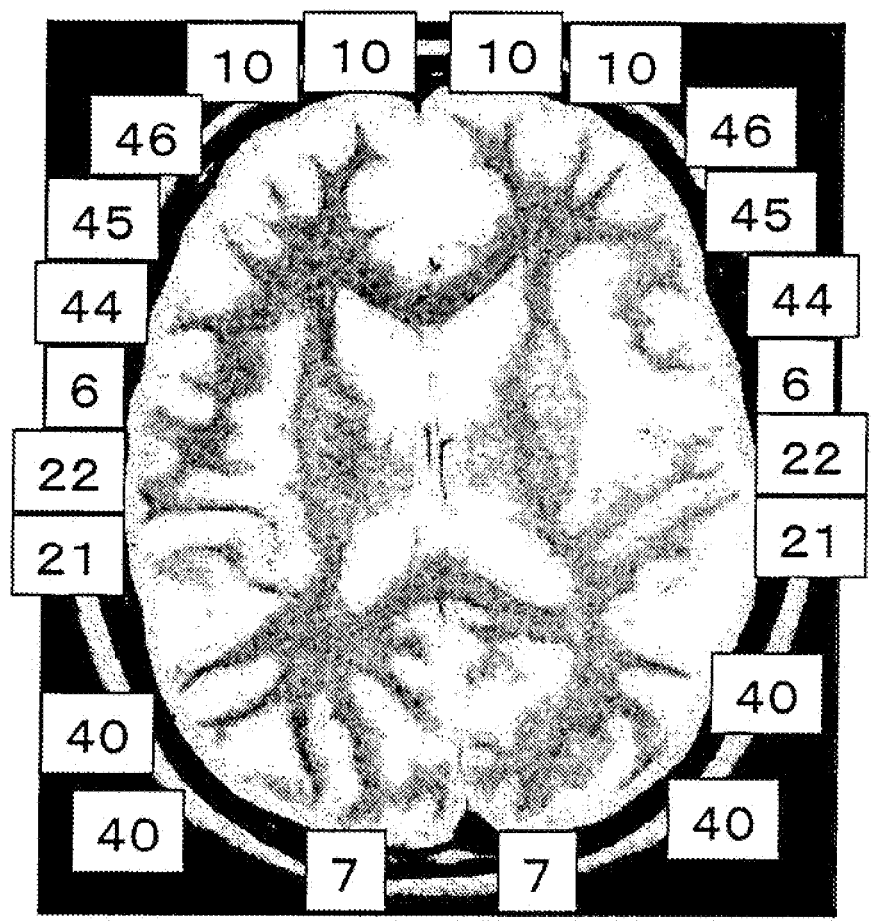
FIG. 4 is an explanatory view showing an example in which addresses for demarcating regions of the brain are displayed together with a white-matter-enhanced image.

FIG. 4 is an explanatory view showing an example in which addresses for demarcating regions of the brain are displayed together with a white-matter-enhanced image. Here, addresses for demarcating regions of the brain are explained. The present inventor has already applied for a patent for the invention of these addresses for demarcating regions of the brain (Japan Patent Application No. 2006-194357.

Explanation of Addresses for Demarcating Regions of the Brain

Figure 5:
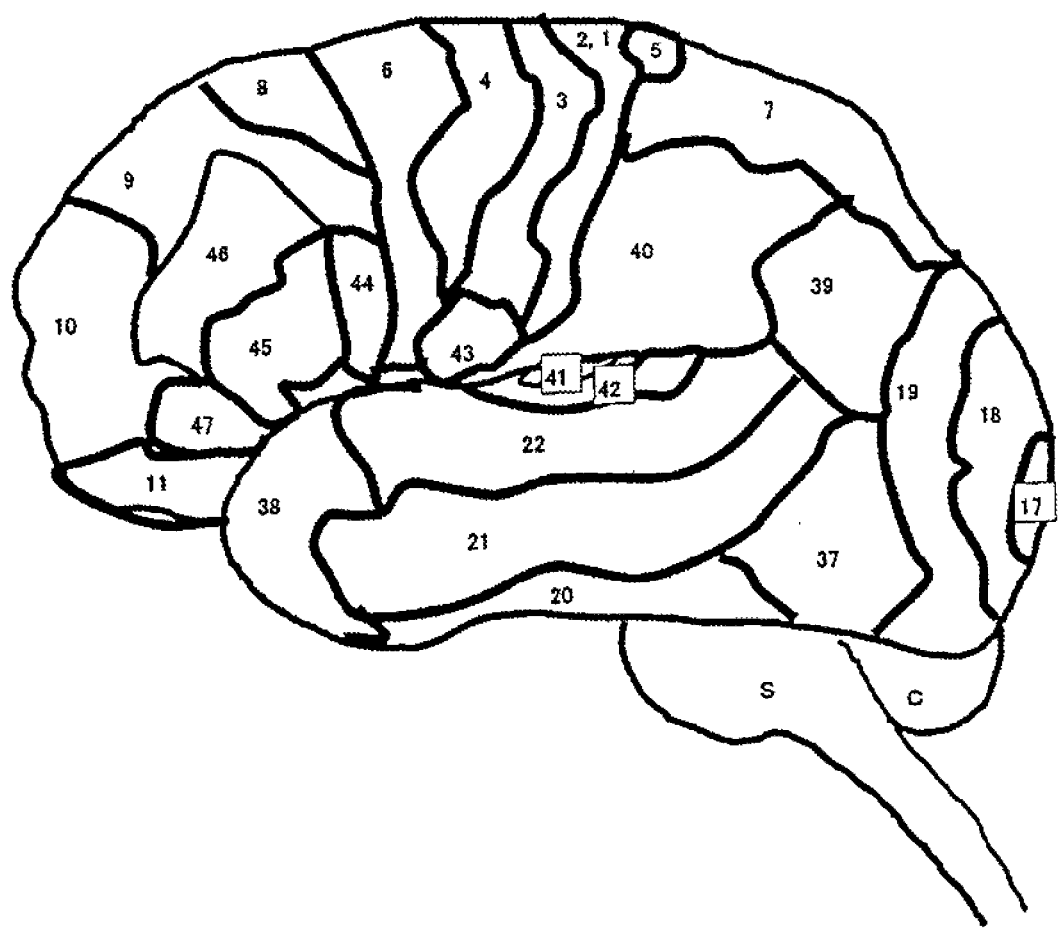
FIG. 5 is an explanatory view in which brain addresses are applied to a 2-dimensional drawing of the brain seen from the outside.
Figure 6:
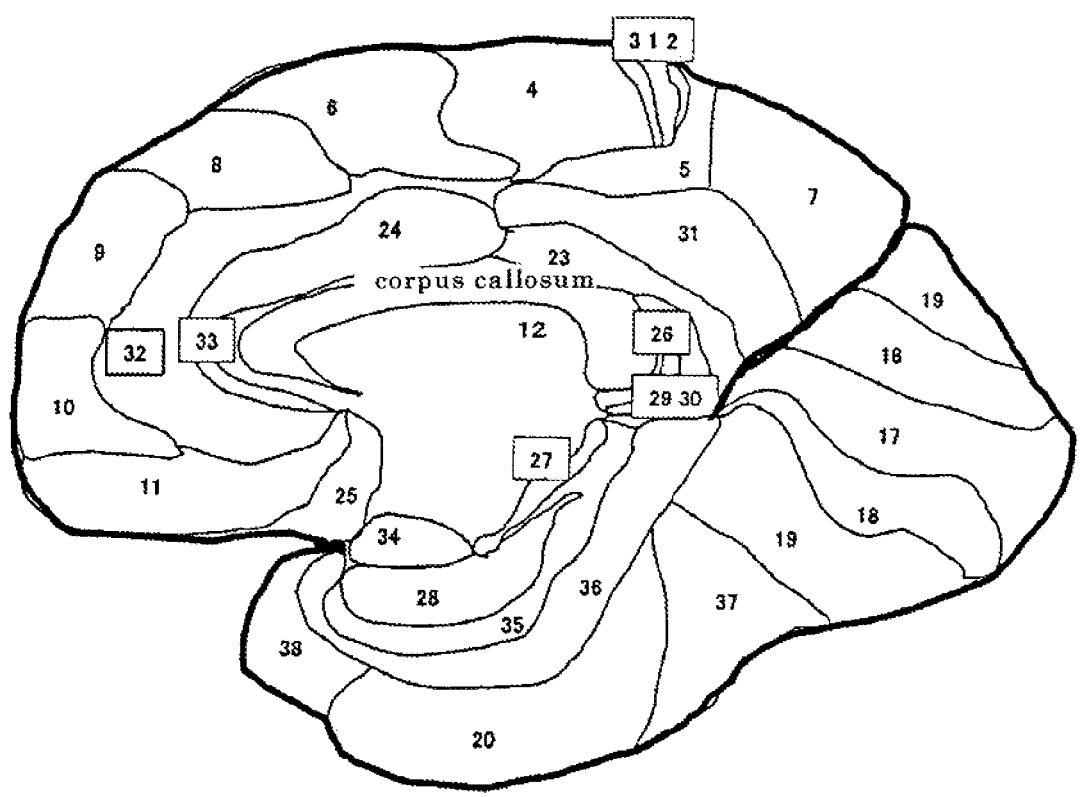
FIG. 6 is an explanatory view in which brain addresses are applied to a 2-dimensional drawing of the brain seen from the inside.
Figure 7:
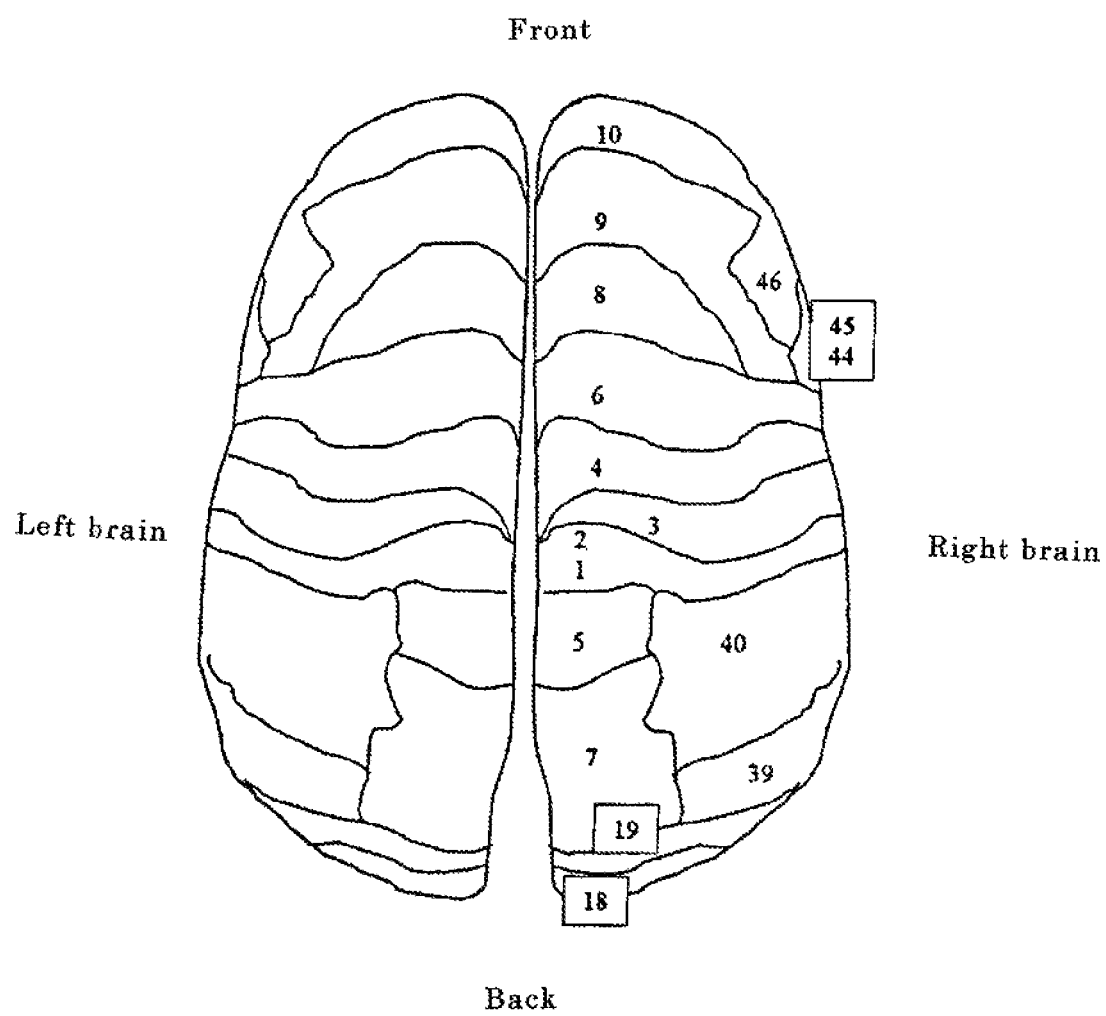
FIG. 7 is an explanatory view in which brain addresses are applied to a 2-dimensional drawing of the brain seen from directly above.
Figure 8:
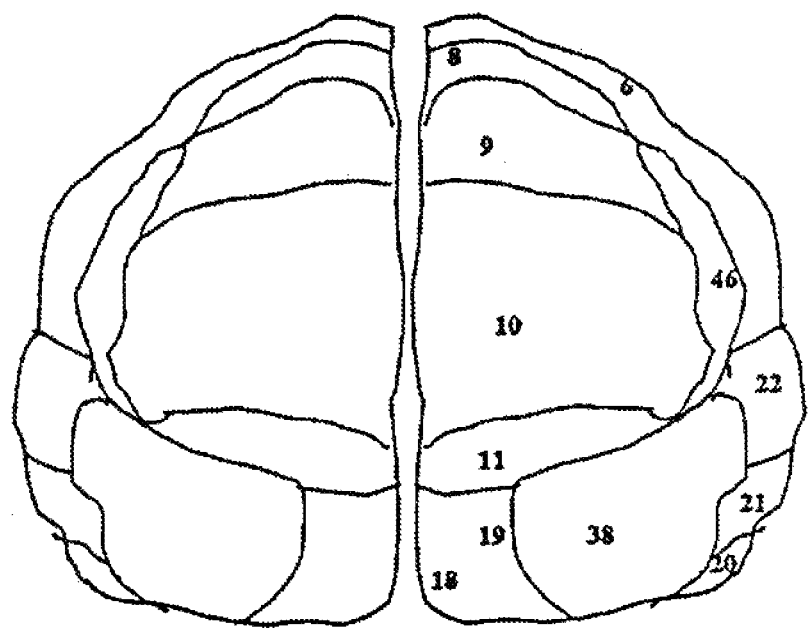
FIG. 8 is an explanatory view in which brain addresses are applied to a 2-dimensional drawing of the brain seen from the front.
Figure 9:
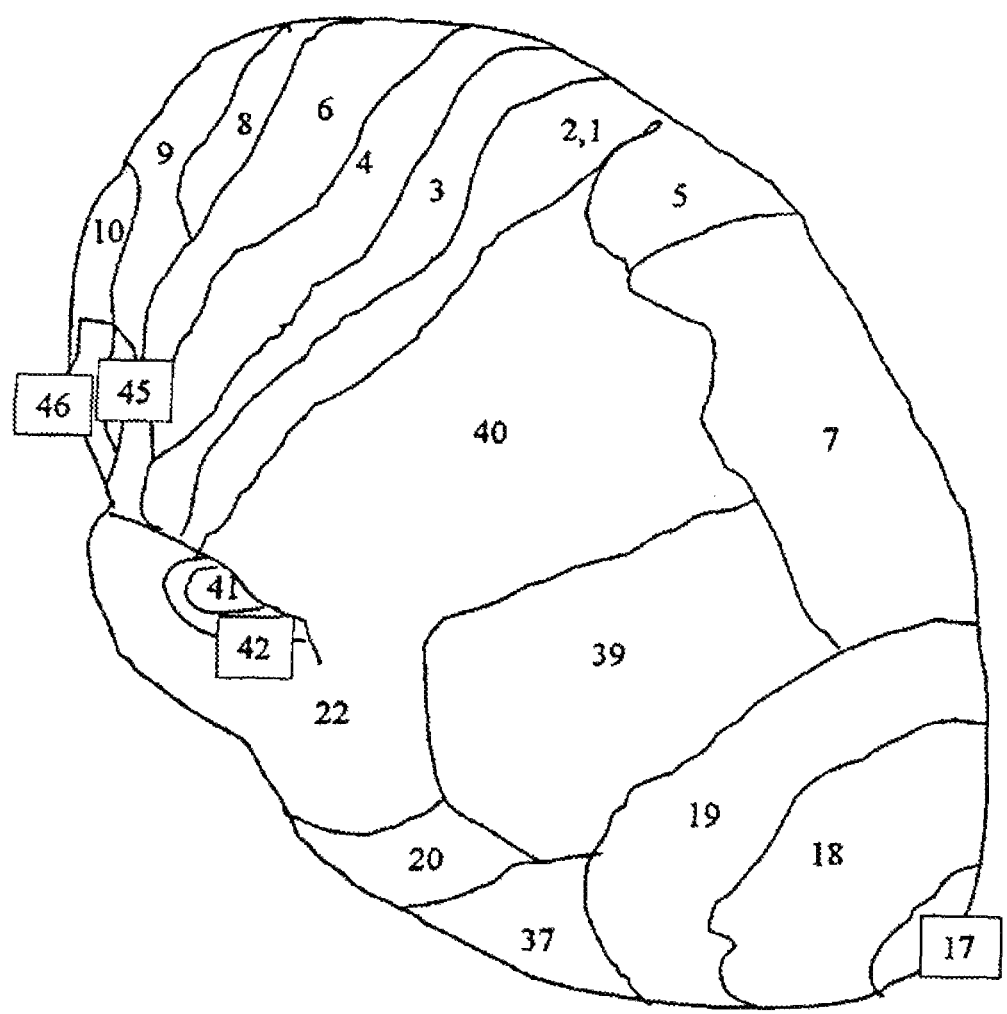
FIG. 9 is an explanatory view in which brain addresses are applied to a 3-dimensional drawing of the brain seen from the left back.
Figure 10:
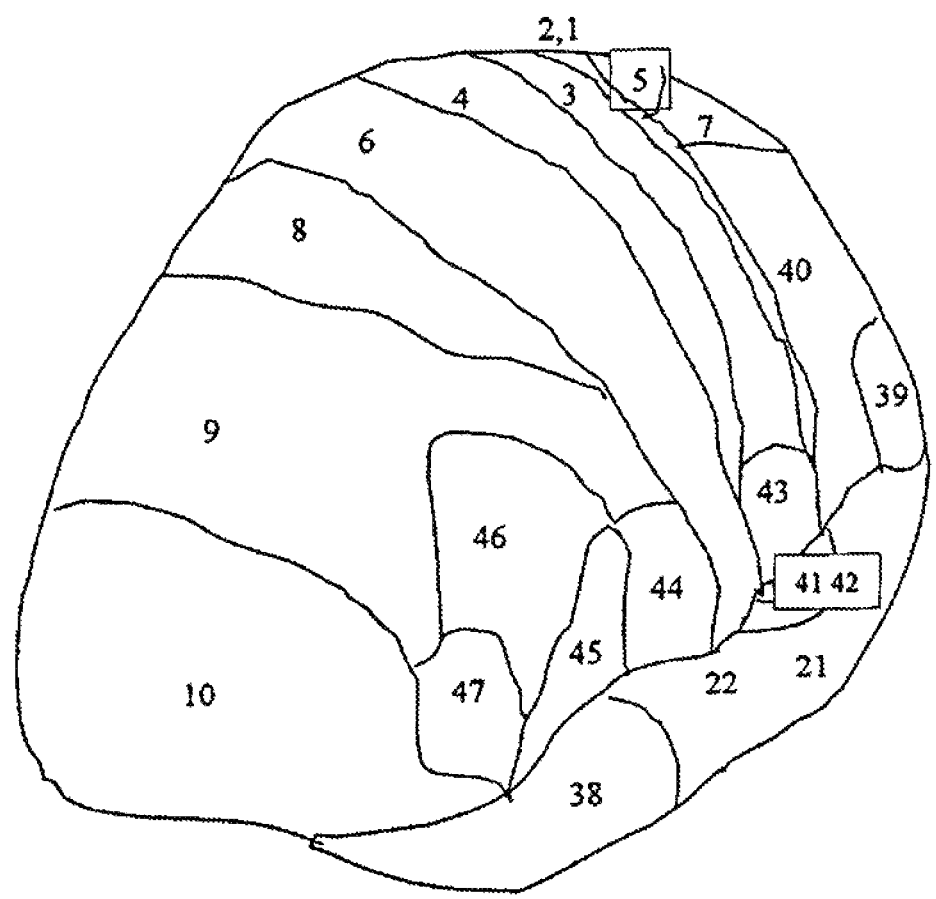
FIG. 10 is an explanatory view in which brain addresses are applied to a 3-dimensional drawing of the brain seen from the left front.
Figure 11:
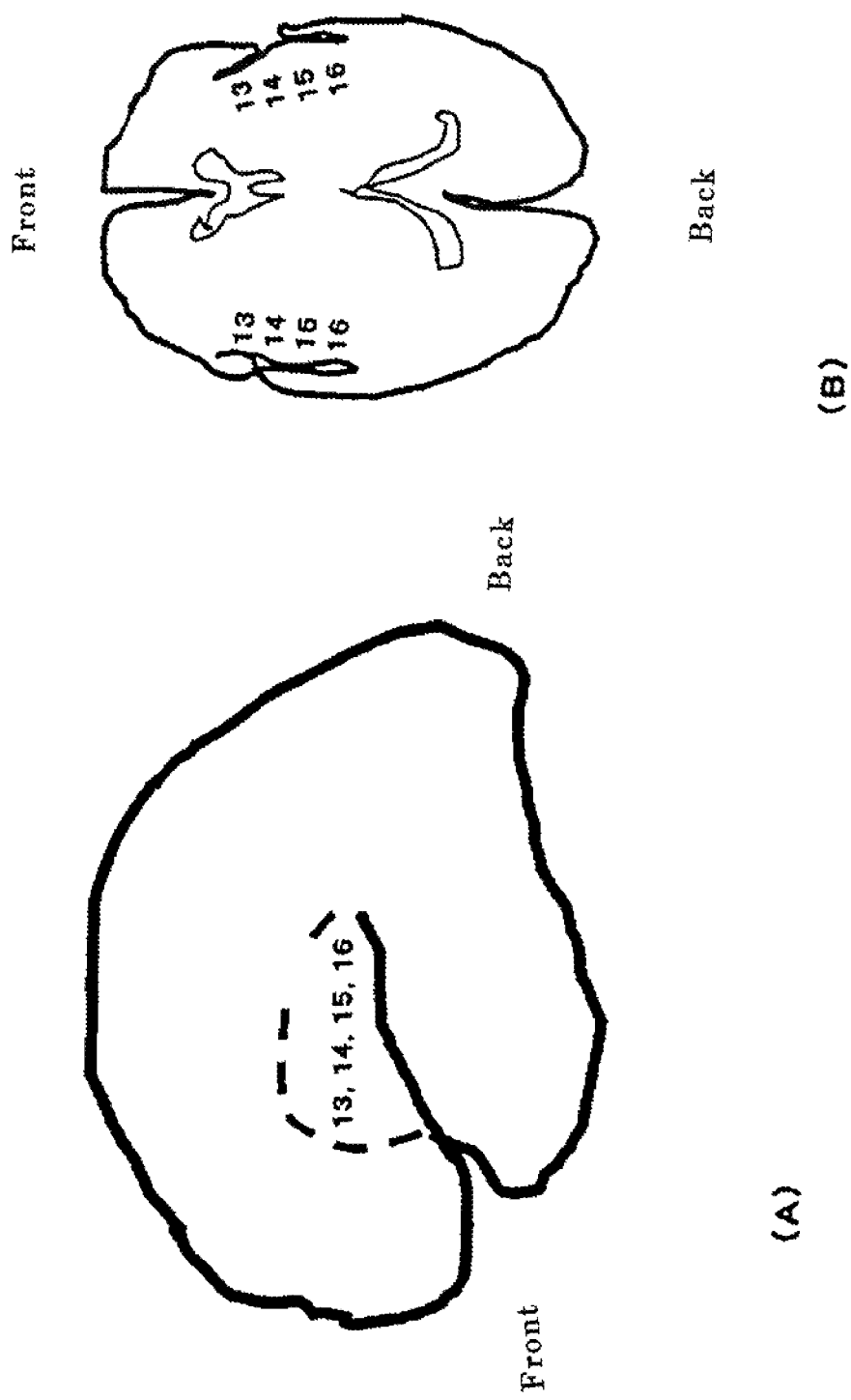
FIG. 11(A) is an explanatory view in which brain addresses are applied to an external side view, and (B) is an explanatory view in which brain addresses are applied to a horizontal cross-sectional view.

FIG. 5 is an explanatory view in which brain addresses are applied to a 2-dimensional drawing of the brain seen from the outside; FIG. 6 is an explanatory view in which brain addresses are applied to a 2-dimensional drawing of the brain seen from the inside; FIG. 7 is an explanatory view in which brain addresses are applied to a 2-dimensional drawing of the brain seen from straight above; FIG. 8 is an explanatory view in which brain addresses are applied to a 2-dimensional drawing of the brain seen from the front; FIG. 9 is an explanatory view in which brain addresses are applied to a 3-dimensional drawing of the brain seen from the left back; FIG. 10 is an explanatory view in which brain addresses are applied to a 3-dimensional drawing of the brain seen from the left front; and in FIG. 11, (A) is an explanatory view in which brain addresses are applied to an external side view, and (B) is an explanatory view in which brain addresses are applied to a horizontal cross-sectional view.

As shown in FIGS. 5-11, addresses for demarcating regions of the brain are numbers applied to demarcate sites that perform given functions and roles in the brain.

In the cerebrum, numbers (1-47) are assigned following the distribution map of brain cell structure according to Brodmann (1907). Brain addresses 4 and 3 form the boundary between the frontal lobe and the parietal lobe; numbers 1 and 2 are in a higher position in the head (see FIG. 7), and numbers are assigned to the front and back around these numbers. Numbers 13-16 form the insular cortex (see FIG. 11).

Figure 12:
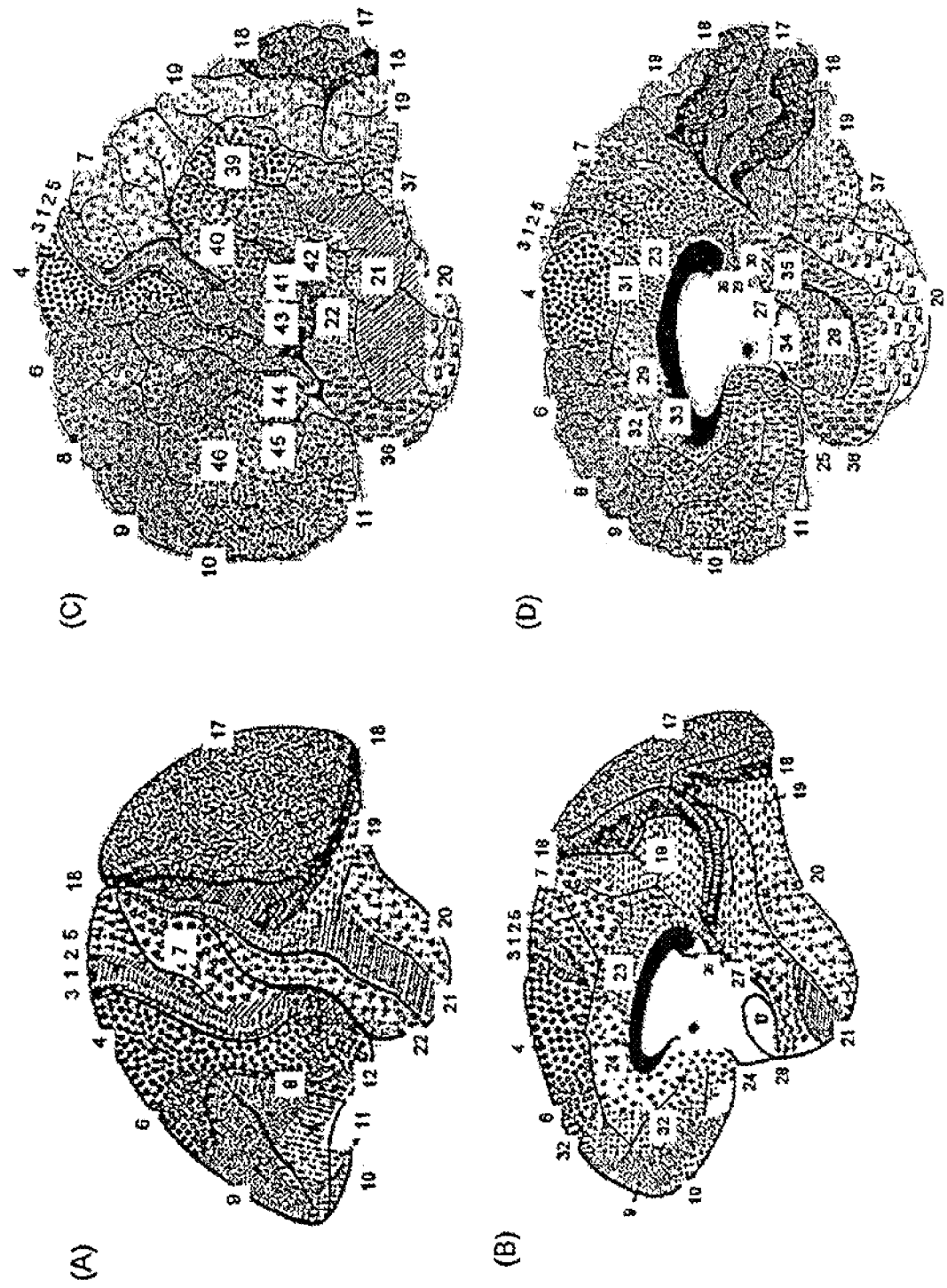
FIG. 12(A) is a brain cell distribution map of a monkey brain, seen from the outside; (B) is a brain cell distribution map of a monkey brain, seen from the inside; (C) is a brain cell distribution map of a human brain, seen from the outside; and (D) is a brain cell distribution diagram of a human brain, seen from the inside.
Figure 13:
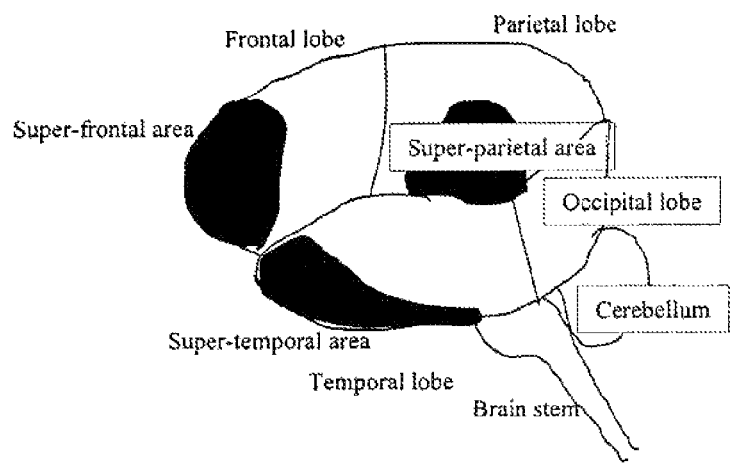
FIG. 13 is an explanatory view showing the super-brain areas.
Figure 14:
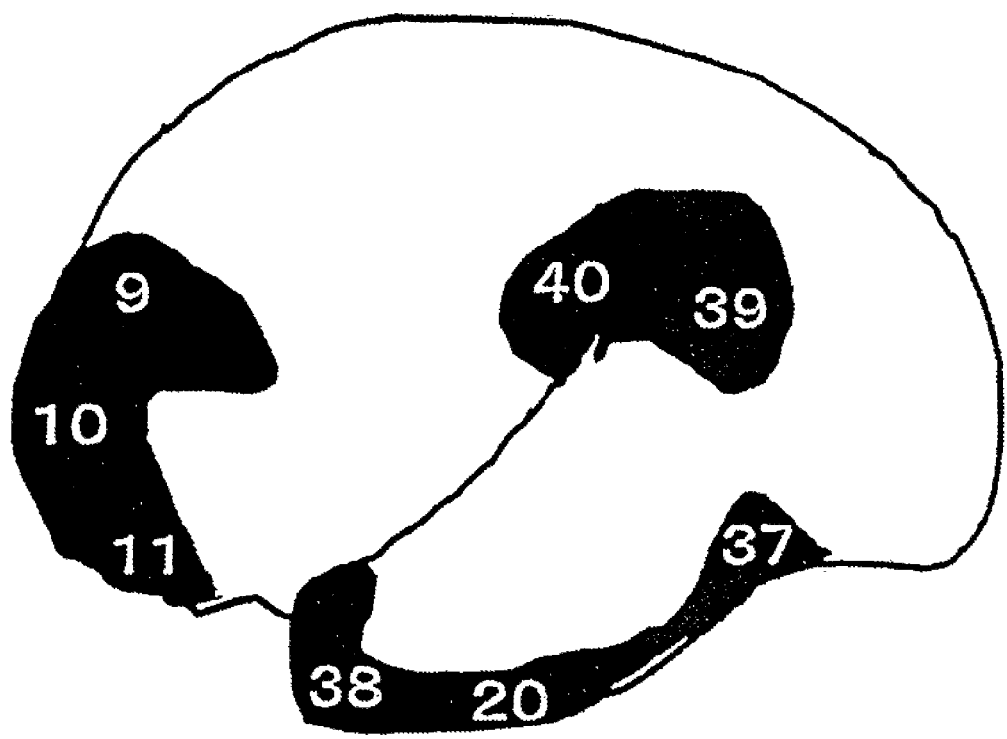
FIG. 14 is an explanatory view showing the relationship between the super-brain areas and the brain addresses.

In FIG. 12, (A) is a brain cell distribution map of a monkey brain, seen from the outside; (B) is a brain cell distribution map of a monkey brain, seen from the inside; (C) is a brain cell distribution diagram of a human brain, seen from the outside; and (D) is a brain cell distribution map of a human brain, seen from the inside; FIG. 13 is an explanatory view showing the "super-brain areas"; and FIG. 14 is an explanatory view showing the relationship between the super-brain areas and the brain addresses.

As can be understood from FIG. 12, the present inventor discovered the fact that when monkey and human brains are compared, there are 3 regions that are particularly developed in humans and are not developed in monkeys.

Among the regions of the brain, these 3 regions were found to correspond to the regions that are the latest to develop. Accordingly, as shown in FIGS. 13 and 14, the present inventor has named these regions the "super-brain areas", and named each of these 3 regions, in the frontal lobe, the parietal lobe and the temporal lobes, the "super-frontal area", the "super-parietal area", and the "super-temporal areas", respectively.

Here, "super-frontal area" applies to the brain addresses 9, 10 and 11; "super-parietal area" applies to brain addresses 39 and 40; and "super-temporal area" applies to 34, 35, 36, 37, 38 and part of 20.

Figure 15:
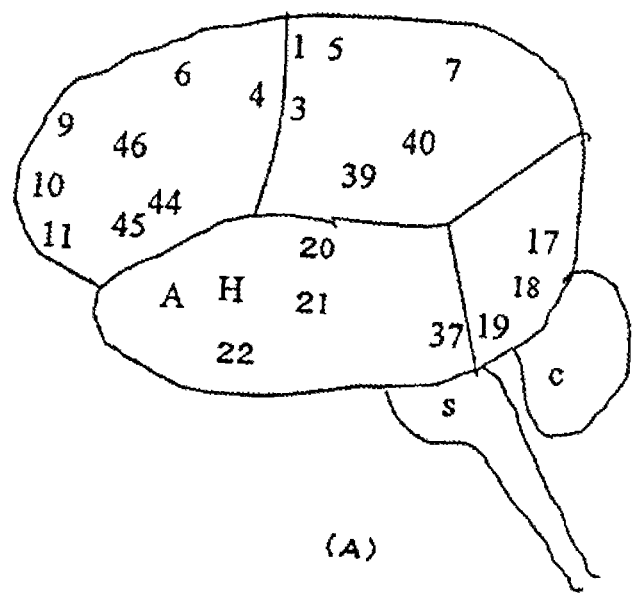
FIGS. 15(A) and (B) are examples of brain address maps; (A) shows the hippocampus (H brain address), the amygdaloid complex (A brain address), the cerebellum (C brain address) and the brain stem (S brain address); (B) shows the thalamus (T brain address); and (C) shows the basal ganglia of the cerebrum (G brain address).
Figure 15:
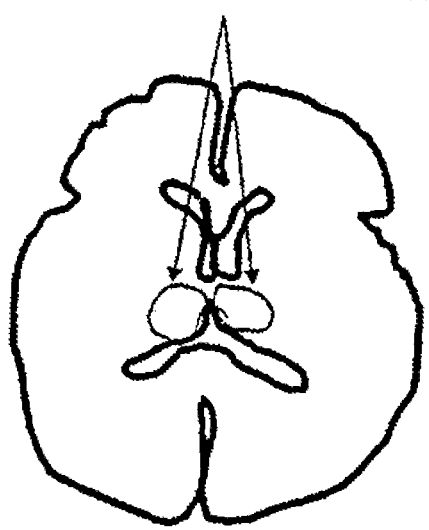
Figure 15:
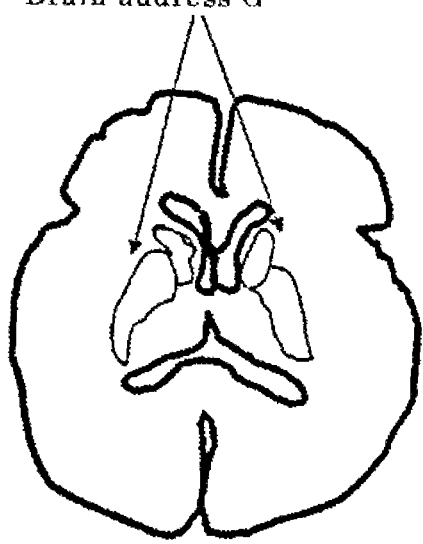

FIG. 15(A) is an example of a brain address map showing the hippocampus (H brain address), the amygdaloid complex (A brain address), the cerebellum (C brain address) and the brain stem (S brain address). FIG. 15(B) shows the thalamus (T brain address), and FIG. 15(C) shows the basal ganglia of the cerebrum (G brain address).

Relationships between the brain addresses and brain sites, functions and roles are as follows:

(1) Frontal Lobe
a) Brain addresses: 4, 6, 8, 9, 32, 33, 24, 44, 45, 46, 10, 11
b) Main functions/roles:
Center of will; integrates communication from various other sites. Has spontaneous will as regards movement, behavior and motor activity; is the location where information is actively accepted, denied and manipulated; other locations support the function of collecting information about sound, shape, motion and the like.
c) Functions/roles of individual brain address sites:
Brain address no. 4: motor: movement of hands, feet, mouth, body muscles; moving, running, jumping, writing, talking Washing a floor, sewing, driving a car.
Left brain no. 4: Writing with the right hand, kicking with the right foot
Right brain no. 4: Writing with the left hand, kicking with the left foot
Brain address no. 6: Planning motor actions; visual imagination; motor action patterns; devising motor actions.
Brain address no. 10: Inability to understand having stolen something; concentration; prediction; detection; thinking deeply and continuously.
Determining hopes. Determination of desires; desire for attention, desire for creativity.

Brain address no. 32: Passive character traits/actions: lack of motivation or attention, not noticing things, lack of interest, lessening of desire or enthusiasm, apathy; character traits/actions showing rapid changes in attention, hyperactivity, too much energy, inability to calm down after excitement, wanting to do everything immediately Brain address nos. 9, 10, 11: Formation of goals; formation of hopes and a sense of mission Brain address no. 11: a brain address that is very sensitive to emotion; development of a social nature Left brain address no. 11: interpersonal understanding through the medium of words; its shape is changed by verbal communication and understanding with another person Right brain address no. 11: non-verbal sociability, interpersonal understanding, understanding another person's unspoken needs or wishes; no. 11 in the right brain cannot be trained just by studying for tests Left brain frontal lobe address nos. 44, 45, 46: Verbal IQ testing, processing speed, verbal working memory, verbal communication Right brain frontal lobe address nos. 44, 45, 46: Nonverbal, graphic IQ test questions, processing speed, nonverbal working memory, nonverbal communication Left brain address no. 45: Manzai (Japanese stand-up comedy dialog), speaking, humming, word imitation/mimicry, person-to-person dialog, conversation, vocalization, sentence composition, speaking words. Internal speech Left brain address no. 44: Vocalization of words Right brain address no. 45, right brain super-temporal area: art-related, manipulation of figures/images, nonverbal-related roles, graphic images, drawing pictures (2) Temporal Lobes a) Brain addresses: nos. 20, 21, 22, 41, 42, 38, 28, 35, the hippocampus (H), the amygdaloid complex (A), the entorhinal cortex (E)

b) Main functions/roles:

Hearing-related information, memory-related storage

The left temporal lobe plays a language-related role; the right temporal lobe, a non-language-related role.

c) Functions/roles of individual brain address sites:

Left super-temporal area:

No. 20: words, conversation, memory, word learning

Hippocampus (H): memory, language acquisition, remembering

Right brain no. 20: site where non-language-related activity information, such as graphic/art-related information, is stored Amygdaloid complex (A): the emotional brain; happiness, sadness, anger, bitterness, comfort, likes/dislikes Brain address nos. 41, 42: sound, listening, basic sound analysis, perfect pitch; the auditory area Brain address no. 22: words, comprehension, music, conversation, listening, kanji (Chinese characters); Wernicke's area; aural comprehension and mechanical repetition ("parroting")

(3) Parietal Lobe a) Brain addresses: nos. 3, 1, 2, 5, 7, 31, 23, 26, 29, 30, 39, 40, 43 b) Main functions/roles:

Spatial grasp of visual information c) Functions/roles of individual brain address sites:

Brain address no. 3: sensation from the hands, feet, body; sense of pressure, skin sensation, algesthesia, pain, sense of temperature; somatosensory area Brain address nos. 1, 2, 5: recognition of information about the location of the body Brain address no. 7: spatial information, games, shapes, moving while looking, depth perception; when vision and motion are required simultaneously Brain address nos. 39, 40: recognizing information; words, comprehension, music, conversation Brain address no. 43: sensation of vibration, rotation (3) Occipital Lobe Brain address nos. 17, 18, 19: understanding forms/patterns; recognition of light and dark, color Brain address nos. 37, 19: moving images, dynamic vision, seeing moving things Brain address no. 17: seeing; light, flash, computer/television screen, movies; static and moving images (5) Cerebellum: instantaneous connection with the cerebrum for fine-tuned feedback control (6) Cerebellum, hippocampus: important in establishing intellectual development The functions/roles of the brain and their corresponding brain addresses are related as follows:

Hearing-related (sound-related) brain addresses: 41, 42, 22, 21

Sight-related brain addresses: 17, 18, 19, 37, 8, 7, 20

Memory-related brain addresses: H, A, 20, 38, 27, 28

Sports-related, motor brain addresses: 32, 4, 6, 8, 17, C

Language-related humanities/social science-related and science-related brain addresses: left brain 44, 45, 46, 22, 39, 40, etc.

Arts-related brain addresses: right brain 44, 45, 46, 22, 39, 40, etc.

Thought-related brain addresses: 10, 9, 11, 46, 39, 40

Emotional and sensory-related brain addresses: 11, 31, H, A

In this way, the brain is divided up into areas, taking into consideration simultaneously the sites (regions) of the brain and their functions/roles, and while referencing the classification according to Brodmann, and the brain addresses are the numbers and letters given to each of these areas.

By dividing the brain by means of brain addresses, the following effects can be achieved.

1) By defining these brain addresses, because they are demarcated based on the shape of the brain and take into consideration not only the different types of cells, but also brain development and growth, and differences between monkeys and humans, it becomes possible to roughly identify localized functional regions of the cerebrum, even if examination of the shape of the brain by MRI and the like cannot differentiate between different types of brain cells.

2) Development of the brain address regions can be considered.

3) Because locations of the brain are assigned addresses, they become easier to remember and understand. If they form pairings with roles or functions, the demarcations on the surface of the brain shown by the brain addresses need not necessarily be inflexible. If new findings are added, revisions and additions are possible.

Displaying brain addresses makes it possible, even when the window level is low, to quickly tell which brain addresses shows the blackest branching.

Or, it is possible to tell which brain addresses does not become black even when the window level is high.

The brain address list (invention of Japan patent application no. 2006-194357, applied for by the present inventor) is matched to the brain addresses of the subject; and because well-developed branches and underdeveloped branches can be distinguished from the branching of the brain, the functions of those branches can be judged to be strengths and weaknesses of the subject.

In addition, this is not necessarily limited to single brain addresses, and networking between relevant brain addresses can thus be judged to be well developed if the blackest branches are interconnected.

Analysis of Distinguishing Brain Characteristics

After that, the distinguishing characteristics of the brain of the living body are analyzed (Step S4), based on the branching of the white-matter-enhanced images created (for example, the number, thickness, length, location, intensity, shape or size of the branches, or a combination thereof).

Figure 16:
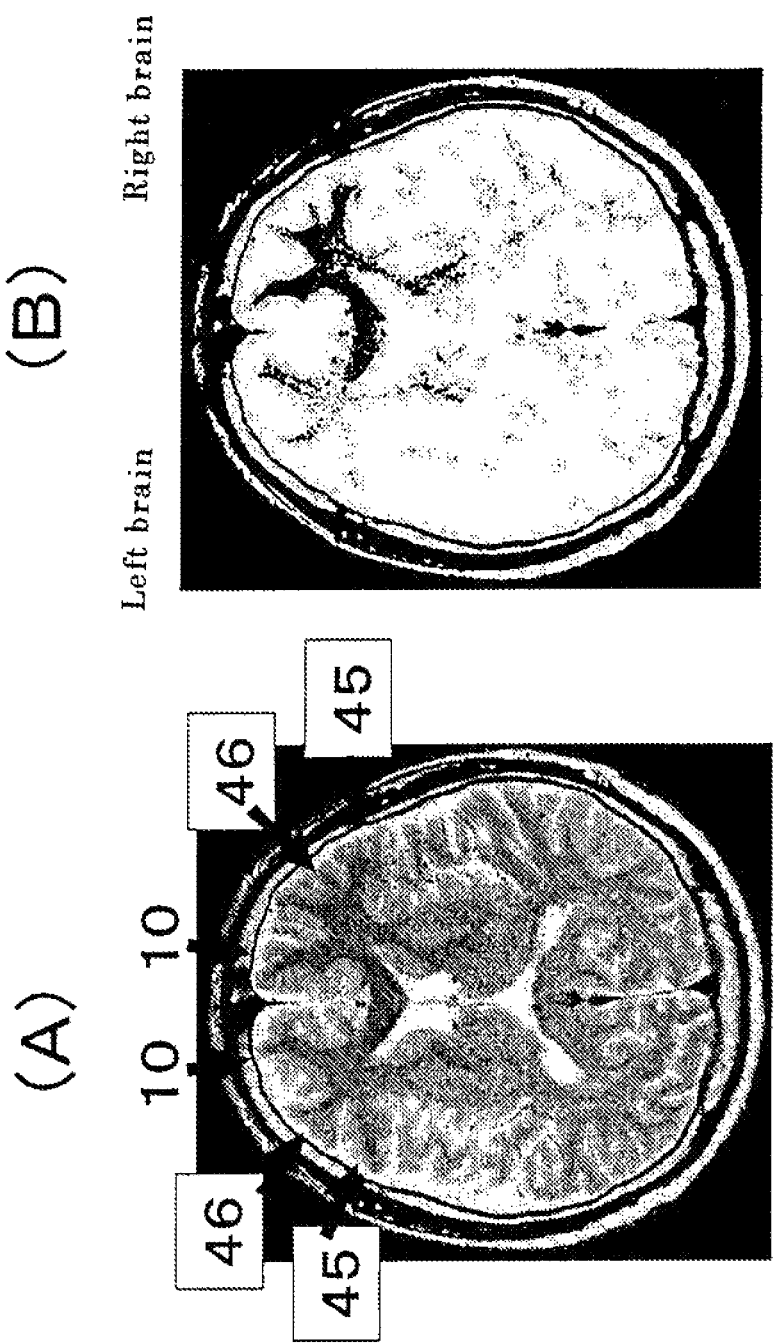
FIG. 16(A) shows a T2-weighted image, and (B) shows a corresponding white-matter-enhanced image.

FIG. 16(A) shows a T2-weighted image, and (B) shows the corresponding white-matter-enhanced image. As shown in FIG. 16(B), because the corpus callosum and left and right brain address nos. 10 are taken as a benchmark, left/right frontal lobe dominance can be decided both qualitatively and quantitatively.

Namely, because the branches in no. 10 of the right brain are thick and dark, while the branches in no. 10 of the left brain have already turned white at this window level, the right brain can be seen to be dominant. In addition, because brain addresses 46 and 45 are dominant on the right and thinner and lighter-colored on the left, we can judge that the subject is better at non-verbal work than at language-related work.

Figure 17:
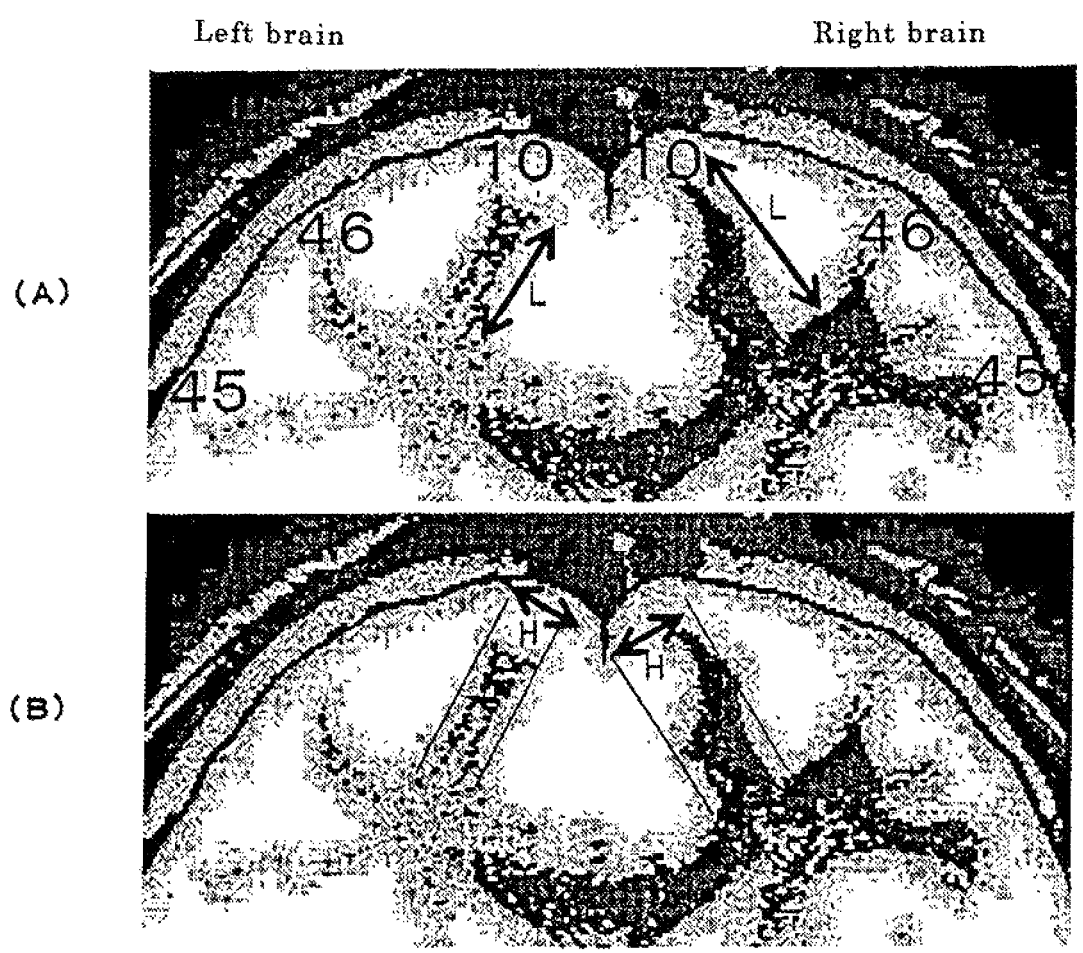
FIGS. 17(A) and (B) are explanatory views for explaining a quantitative measurement method for use in white-matter-enhanced images.

FIGS. 17(A) and (B) are explanatory views for explaining a quantitative measurement method for use in white-matter-enhanced images. Branch length L, as shown in FIG. 17(A), is measured for each of nos. 10, 46 and 45, left and right. Branch width (thickness) H, as shown in FIG. 17 (B), is also measured for each of nos. 10, 46 and 45, left and right.

Figure 18:
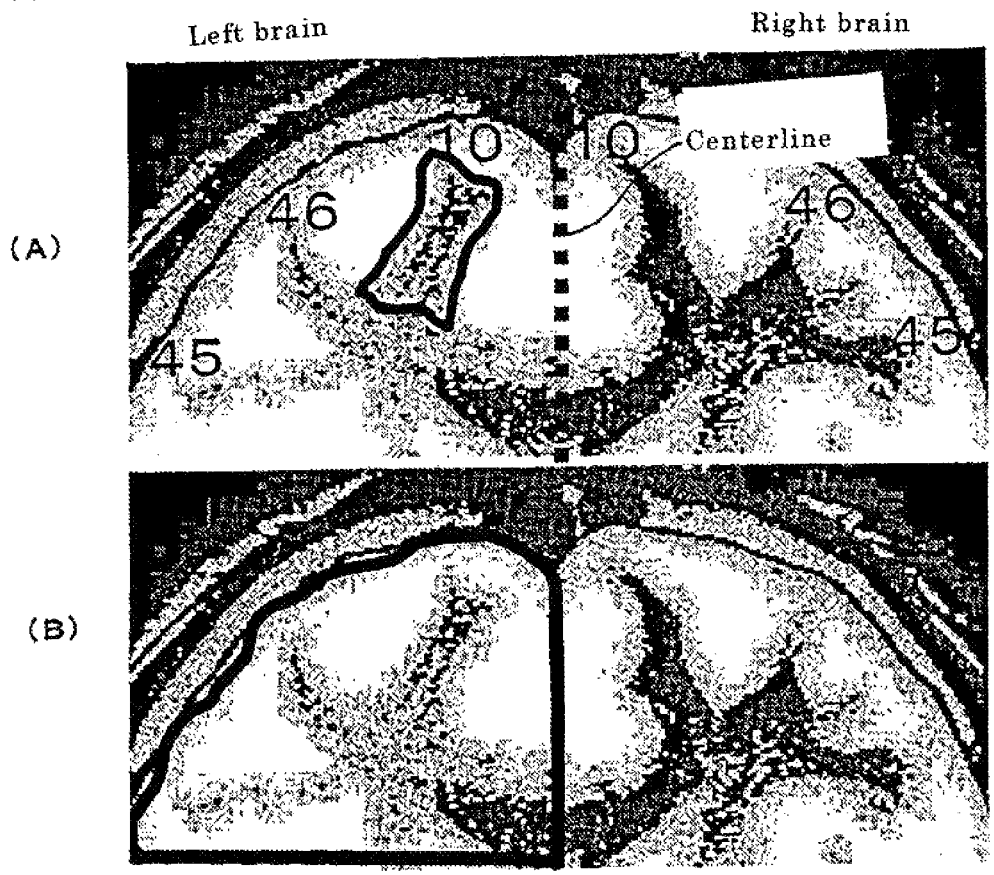
FIGS. 18(A) and (B) are explanatory views for explaining a quantitative measurement method for use in white-matter-enhanced images.

FIGS. 18(A) and (B) are explanatory views for explaining a method for quantitative measurement in white-matter-enhanced images. The number of black pixels is counted for each or all addresses, divided by the centerline, as shown in FIG. 18(A), to calculate the surface area or, taking the image thickness into consideration, the volume of the left and right white matter. In addition, the black/white density is calculated for the surface area or, taking the image thickness into consideration, the volume of white matter, for an arbitrary left/right facing region, divided by the centerline, as shown in FIG. 18(B).

Figure 19:
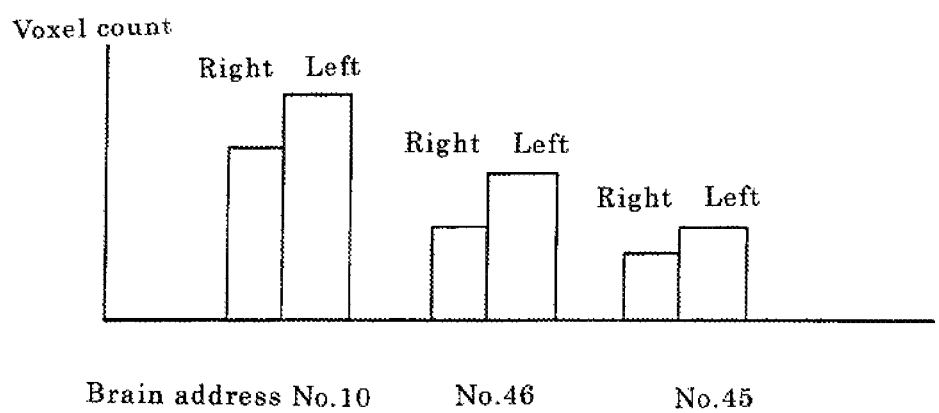
FIG. 19 is a graph showing number of voxels (volumetric pixels) in the white matter portion of the right and left brain for brain addresses in a white-matter-enhanced image.

FIG. 19 is a graph showing the number of voxels (volumetric pixels) in the white matter portion of the right and left brain for brain mapping addresses in a white-matter-enhanced image. To compare left and right brain dominance, if we take the number of voxels (volume) in the branches in the right brain addresses to be R, and the number of voxels in the branches in the left brain addresses to be L, then a Laterality Index (LI) can be calculated by the equation:

$$(R-L)/(R+L)=LI$$

LI moves between −1 and +1. If LI is negative, left brain dominance is strong, and if it is positive, right brain dominance is strong.

Figure 20:
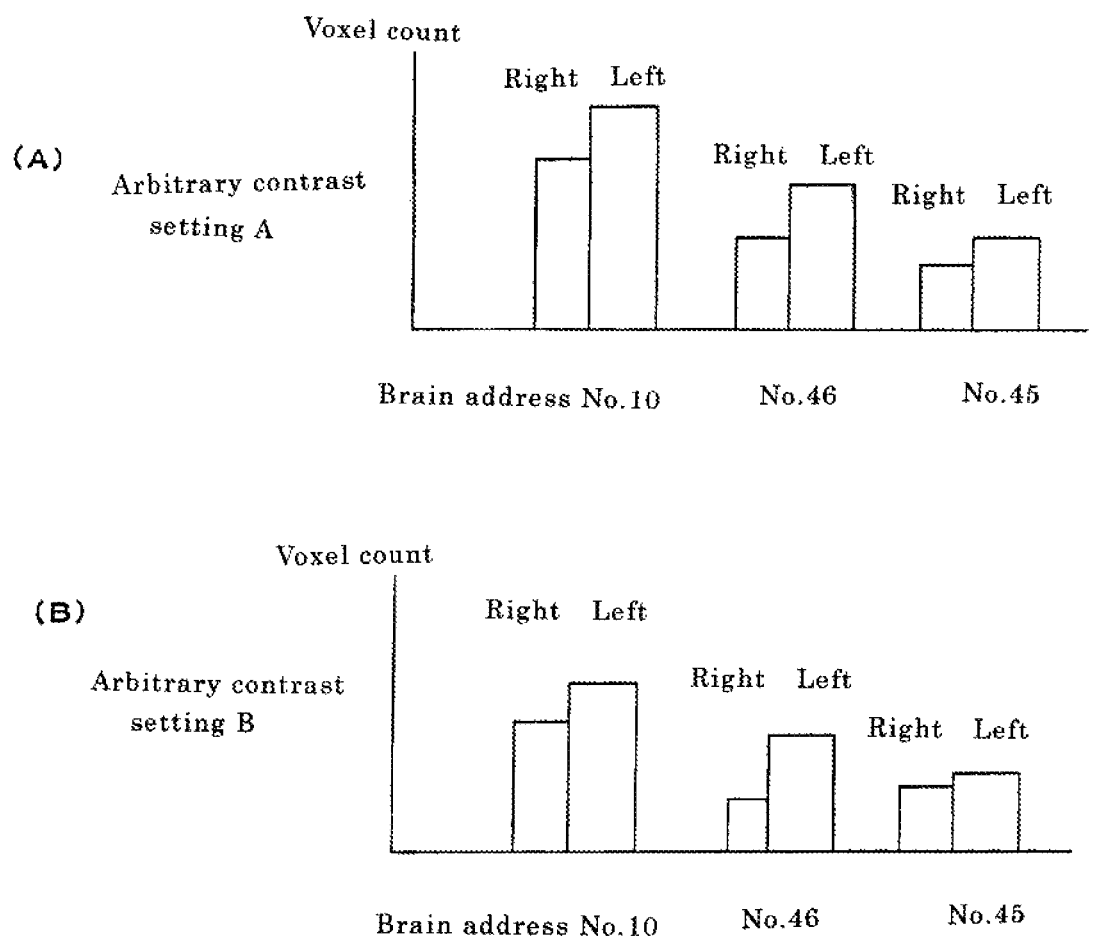
FIG. 20 is a graph showing number of voxels (volumetric pixels) in the white matter portion of the left and right brain for brain addresses in a white-matter-enhanced image; in (A), the contrast is set at arbitrary contrast A, and in (B), at arbitrary contrast B.

FIG. 20 is a graph showing the number of voxels in the white matter portion of the left and right brain in a white-matter-enhanced image for brain mapping addresses; in (A), the contrast is set at arbitrary contrast A, and in (B), at arbitrary contrast B.

As shown in FIGS. 20(A) and (B), quantitative displays can be made for arbitrary contrast settings. Namely, the contrast ratio (W/C)=E, between the cortex (C) and the white matter (W), can be adjusted by changing WW (window width) and WL (window level). By varying the contrast ratio E and drawing contours differentiated by color, branch area and volume ratios can be calculated not only for the entire brain, but also for arbitrarily selected brain addresses.

Figure 21:
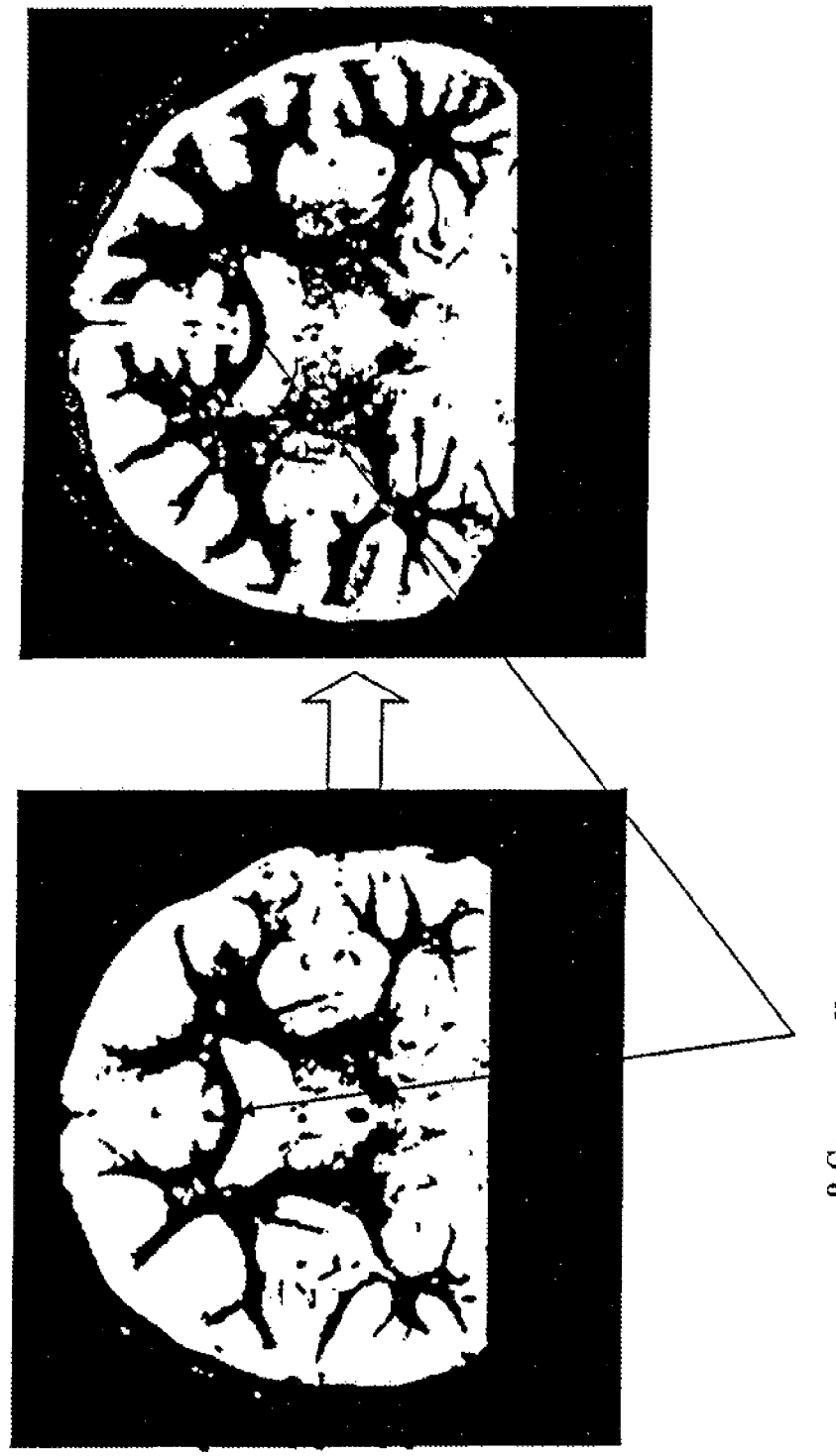
FIG. 21 is an explanatory view showing an example in which brain branching from two contrast MRI images obtained at different times is compared quantitatively.

FIG. 21 is an explanatory view showing an example in which brain branching from two contrast MRI images obtained at different times is compared quantitatively. As shown in FIG. 21, the thickness and shape, etc. of the corpus callosum 9 have changed with growth, but by making the corpus callosum 9, located medially between the left and right brain, the same color, it becomes possible to compare other brain addresses.

Figure 22:
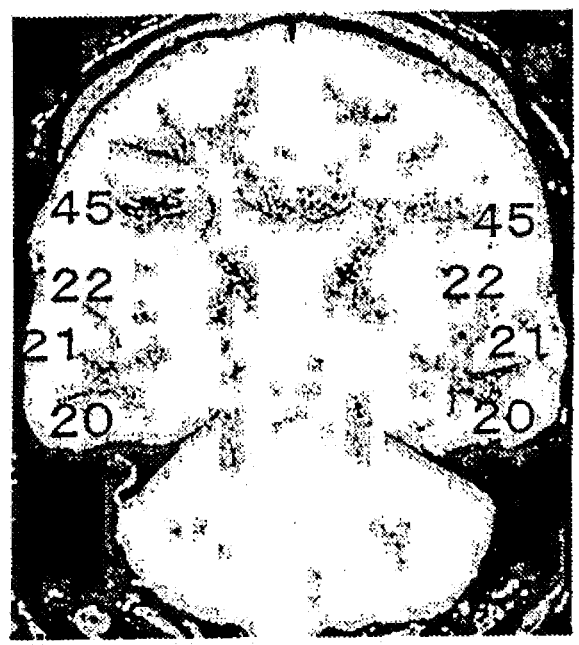
FIG. 22 is an explanatory view for explaining an example of an image showing left/right brain address dominance.

FIG. 22 is an explanatory view for explaining an example of an image showing left/right brain address dominance. As shown in FIG. 22, it can also be made possible to immediately recognize left/right brain address dominance, as in left dominance for address no. 45 and right dominance for address no. 21, by taking either the left or the right of an arbitrary brain address as a benchmark.

Figure 23:
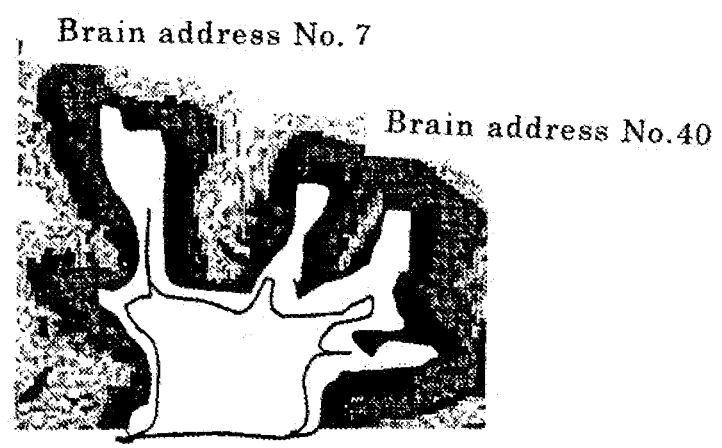
FIG. 23 is an explanatory view for explaining an example of an image displaying brain branching contours.
Figure 24:
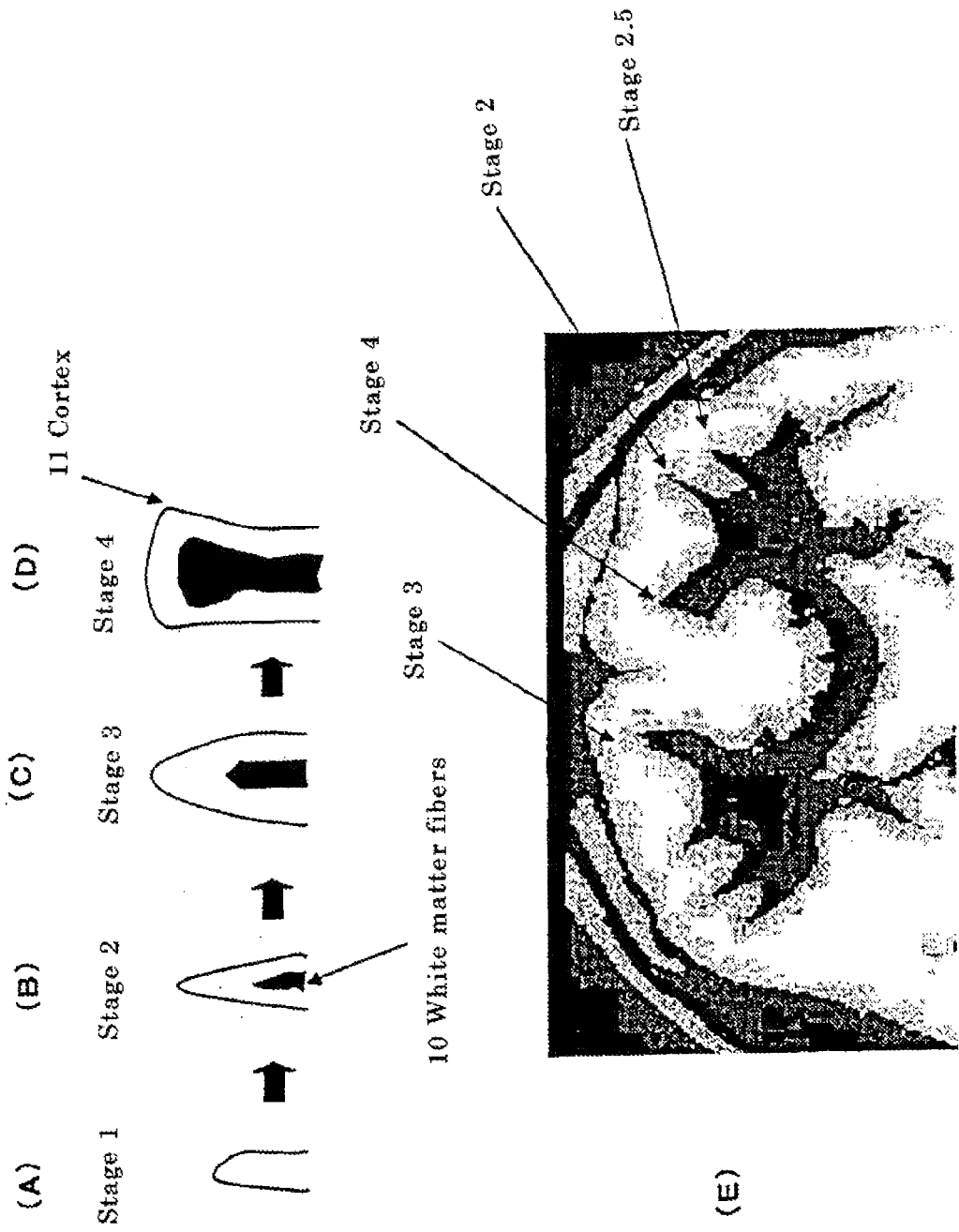
FIG. 24(A) through (D) are explanatory views for explaining an example of classification of brain branching into stages in the process of development and growth of the brain gyms, and (E) is an explanatory view for explaining an example of mapping those stages.

FIG. 23 is an explanatory view for explaining an example of an image displaying brain branching contours. As shown in FIG. 23, displaying the outlines of the white matter branches as their shapes change with changes in window level as contour images or identifying them by color, makes it possible to visually differentiate between brain addresses with good branching and those with bad branching. In addition, by a similar method, by comparing 2 MRIs from the same person at different times, the growth in area and volume of brain address branches can be measured, thus differentiating between branches showing marked growth and branches without growth.

FIGS. 24(A) through (D) are explanatory views for explaining an example of classification of brain branching into stages in the process of development and growth of the brain gyrus, and (E) is an explanatory view for explaining an example of mapping those stages. In FIG. 24, 10 corresponds to white matter fibers, and 11, the cortex. Tips of brain branches are classified as stages 1-4, as shown in FIGS. 24(A) through (D), and by mapping the stages of growth that correspond to that template, as shown in FIG. 24(E), it is possible to convert the state of growth of the branching the entire brain into numerical values.

Namely, first, the stage of each branch is determined, and then the pixel count (image area) or the voxel count (volume), are calculated from the MRI brain image, and the pixel count (or voxel count) is multiplied by the stage number to give a numerical value.

In addition, by mapping the stages of the brain branching, the brain branching growth age can be calculated. For example, if the stages of the gyms development/growth process are set at 10-year intervals, as shown below, stages are mapped for each brain address and those average values are defined as brain branching growth ages:

Stage 1=age 10
Stage 2=age 20
Stage 3=age 30
Stage 4=age 40
Stage 5=age 50

Figure 25:
FIG. 25(A) is a T2-weighted image showing a sagittal cross-section of a brain; (B) and (C) are images that make visible the differences between branching in the corpus callosum.

FIG. 25(A) is a T2-weighted image showing a sagittal cross-section of a brain; (B) and (C) are images that make visible the differences between branching in the corpus callosum. The connections between the branching of the different lobes can be seen in FIG. 25(C): the genu 12 of the corpus callosum connects between the brain addresses of the frontal regions in the front of the head, the splenium 13 connects between the brain addresses of the occipital lobe, and the body of the corpus callosum connects brain addresses of the frontal lobe and the parietal lobe.

Figure 26:
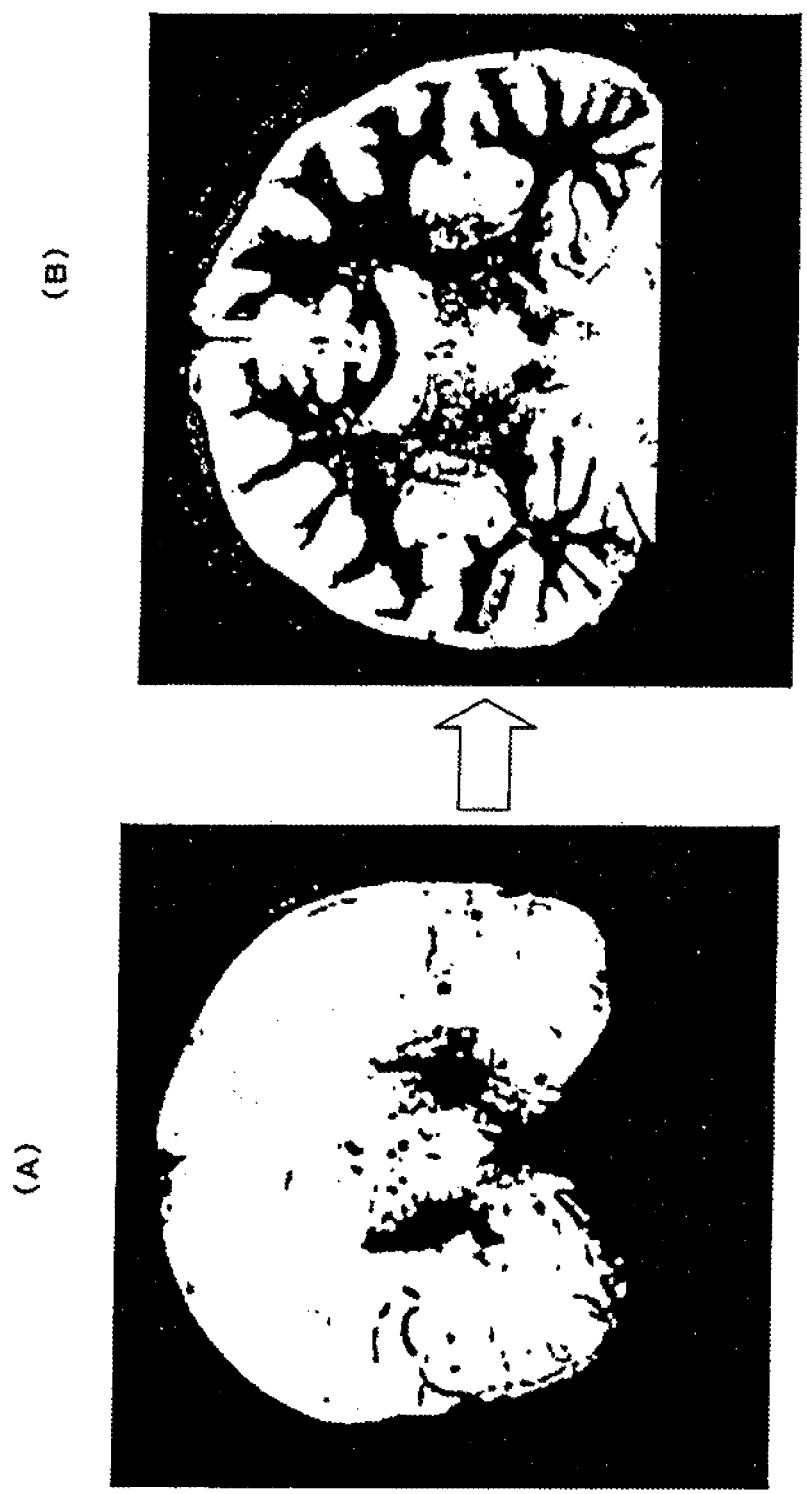
FIGS. 26(A) and (B) are explanatory views showing white-matter-enhanced images that show the growth of brain branching.

FIGS. 26(A) and (B) are explanatory views showing white-matter-enhanced images that show the growth of brain branching. By taking the cerebral basal ganglia and the thalamus are taken as a benchmark, it becomes easy to differentiate brain branching growth, even between different individuals, as shown in FIGS. 26(A) and (B).

Figure 27:
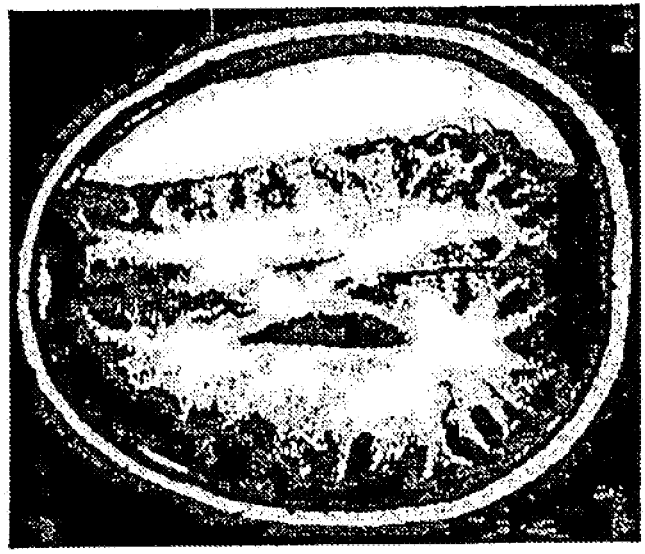
FIG. 27(A) is an explanatory view showing a T1-weighted image with a lesion, and (B) is an enhanced image in which the lesion is white, the cortex is black and the white matter branching is white.
Figure 27:
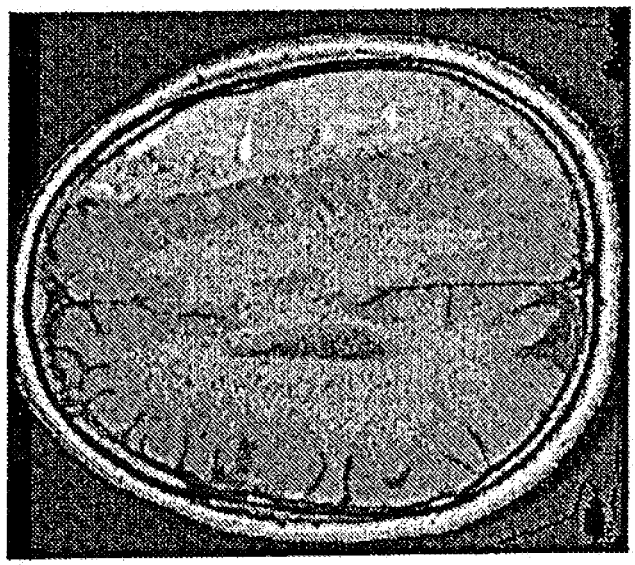

FIG. 27 is explanatory views showing (A), a T1-weighted image with a lesion, and (B), an enhanced image in which the lesion is white, the cortex is black and the white matter branching is white. As shown in FIG. 27(B), by making the lesion white as a benchmark, distortion of the branches becomes visible at a glance. In addition, the lesion can be seen to be pressing on the white matter branches.

Figure 28:
FIG. 28(A) is an explanatory view showing a FLAIR-weighted image with a lesion, and (B) is a branching-enhanced image in which the lesion is white, the cortex is white and the white matter is made black.
Figure 28:

FIG. 28 is explanatory views showing (A), a FLAIR-weighted image with a lesion, and (B), a branching-enhanced image in which the lesion is white, the cortex is white and the white matter is made black. As shown in FIG. 28 (B), by making the lesion white as a benchmark, distortion of the branches becomes visible at a glance. In addition, the lesion can be seen to be pressing on the white matter branches.

Figure 29:
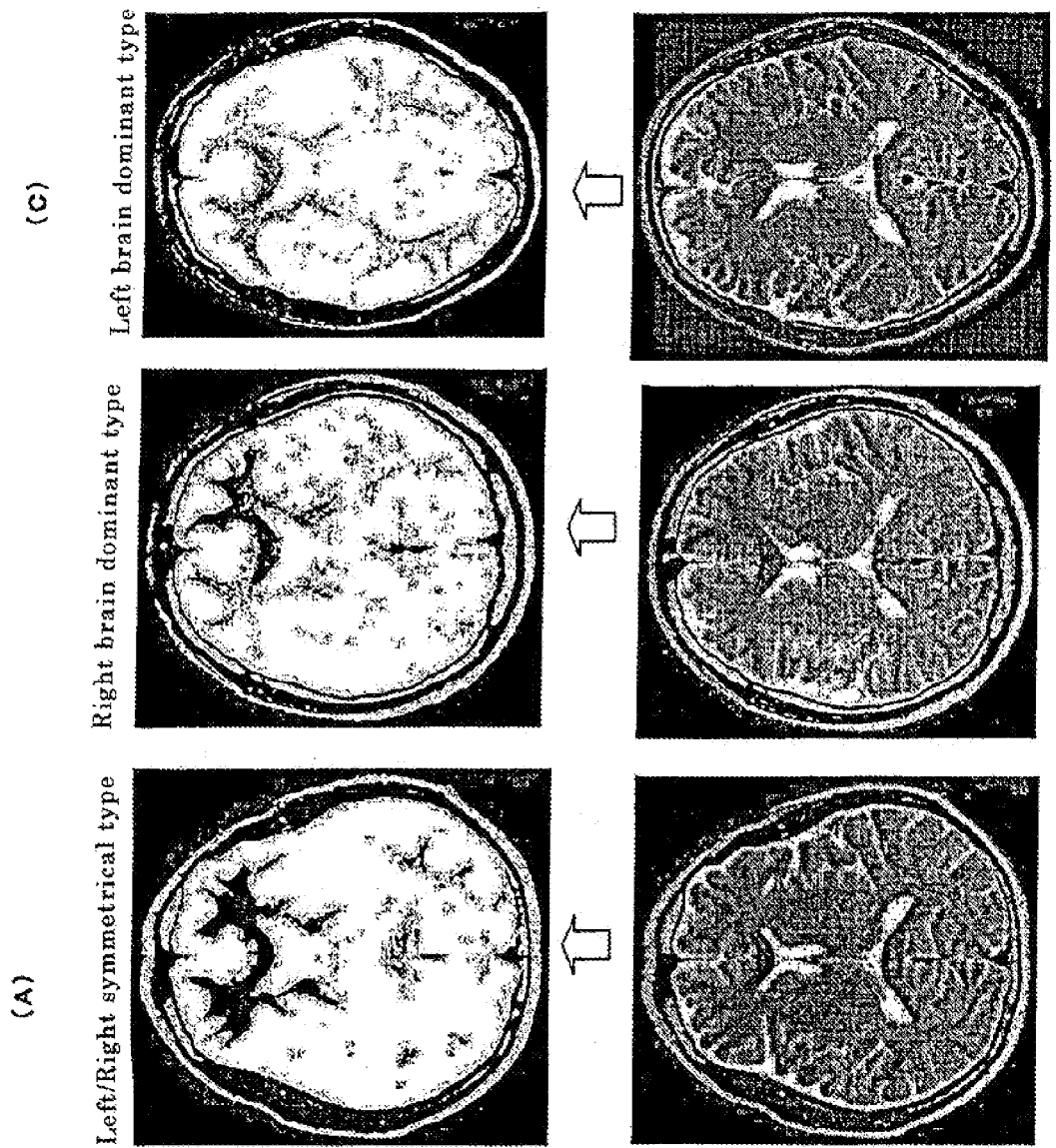
FIG. 29 are Explanatory views for explaining the determination of frontal lobe dominance, utilizing a white-matter-enhanced (branching-enhanced) image of the brain. The images in the lower row are T2-weighted images, and in the upper row, white-matter-enhanced images; (A) is a case of left/right brain symmetry; (B), a case of right brain dominance; and (C), a case of left brain dominance.

FIG. 29 is an explanatory view for explaining the determination of proximal lobe dominance utilizing white-matter-enhanced (branching-enhanced) images of the brain; the images in the bottom row are T2-weighted images; and those in the upper row, white-matter-enhanced images: in (A), the left and right hemispheres are symmetrical; in (B), the right brain is dominant; and in (C), the left brain is dominant.

Previously, in 2003, Dr. Toga and Dr. Thompson of UCLA, in the journal "Nature Neuroscience" [Reviews], performed statistical image analysis on the morphology of the brain sulci and showed statistically that the left occipital lobe extends out into the right occipital lobe side and the width of the right frontal lobe is wider than that of the left frontal lobe. It is clear that statistically, the left and right brain are not symmetrical, but have a twisted shape.

Their technique was a group analysis technique using the cortical matter of the cerebrum, which comprises cortical matter and white matter. There was, however, absolutely no examination of group analysis of the white matter.

In contrast, the present inventor does not examine left/right brain differences utilizing the sulci of the cortical matter, but has investigated healthy subjects, using branching of the white matter of the brain as an index.

In doing so, this inventor found that there was individual variation in the branching of the left and right super-frontal regions. Furthermore, after looking at the brains of as many as 50 healthy subjects, this inventor discovered the existence of three types, as shown in FIG. 29: right brain dominant super-frontal region branching, left/right symmetrical branching, and left brain dominant super-frontal region branching. This shows that even without injury to a part of the brain addresses, there is individuality in the growth of the brain branches in the growth process. When character tendencies of these 3 groups were analyzed, including prior data, a personality type was recognized in which, in the right super-frontal region branching-dominant type, at least in comparison with the left super-frontal region branching-dominant type, there was difficulty with verbal expression and putting an idea into words, even if the idea was understood. The left/right symmetrical branching type tended to be inflexible in character.

Namely, with this invention, the possibility of analyzing brain individuality was realized because of the fact that group analysis of the white matter was made possible.

Figure 30:
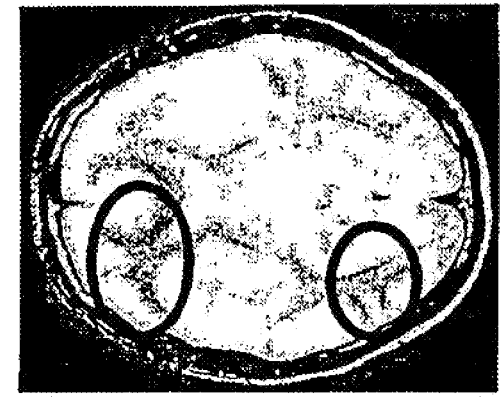
FIG. 30(A) through (C) are explanatory views showing brain address mapping utilizing brain branching images.
Figure 30:
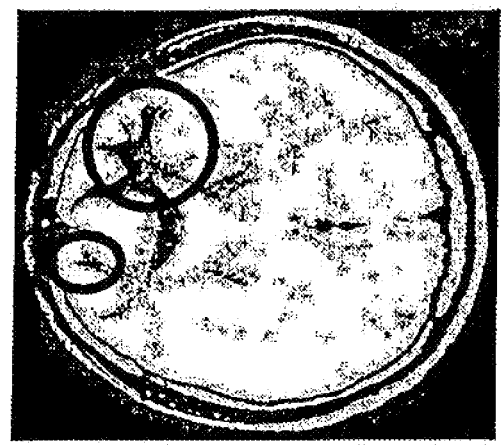
Figure 30:
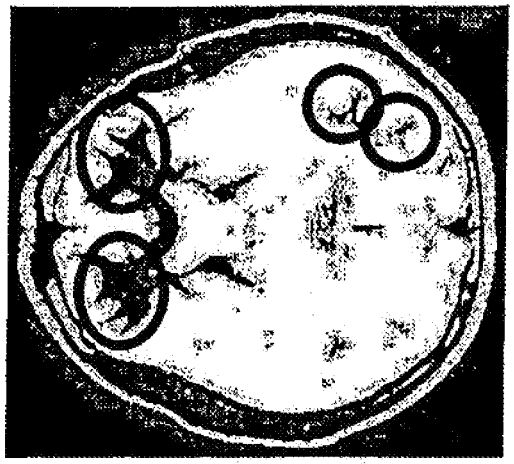
Figure 30:
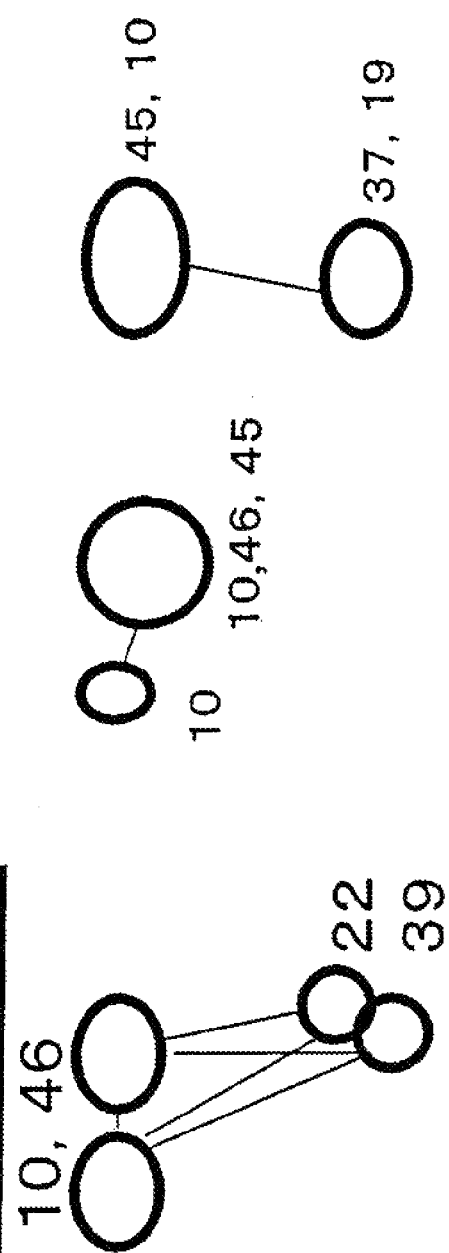

FIG. 30(A) through (C) are explanatory views showing brain address mapping utilizing brain branching images. FIG. 30(A) shows a left/right frontal lobe right brain dominant network, (B) shows a right frontal lobe dominant network, and (C) shows a left brain dominant network.

Figure 31:
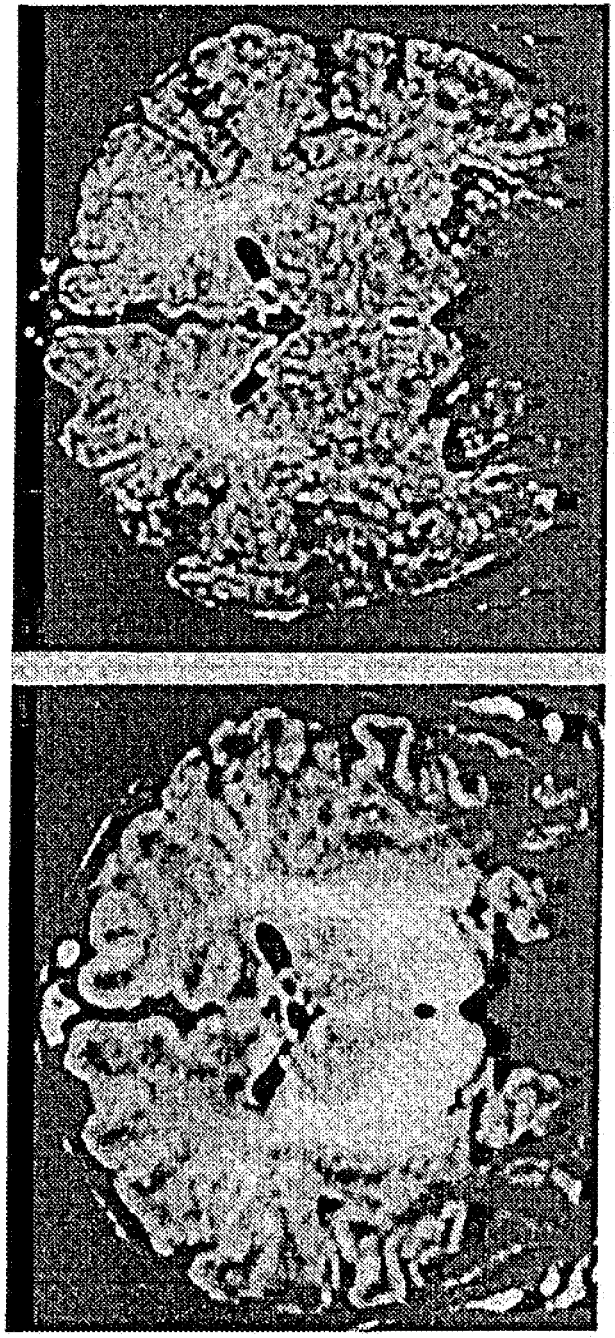
FIG. 31 are explanatory views: (A) shows a FLAIR image (TE=20 ms) of white matter branching; (B) shows a FLAIR image (TE=180 ms) predicting branching growth.

FIG. 31 is explanatory views: (A) shows a FLAIR image (TE=20 ms) of white matter branching, and (B) shows a FLAIR image (TE=180 ms) predicting branching growth. From FIG. 31, it can be seen that by obtaining FLAIR images with a short TE and a long TE while keeping the other conditions the same, images can be obtained that distinguish the stages of branching. The location of the strongest white point can be seen to have moved toward the cortex side of the motor-related brain addresses.

Figure 32:
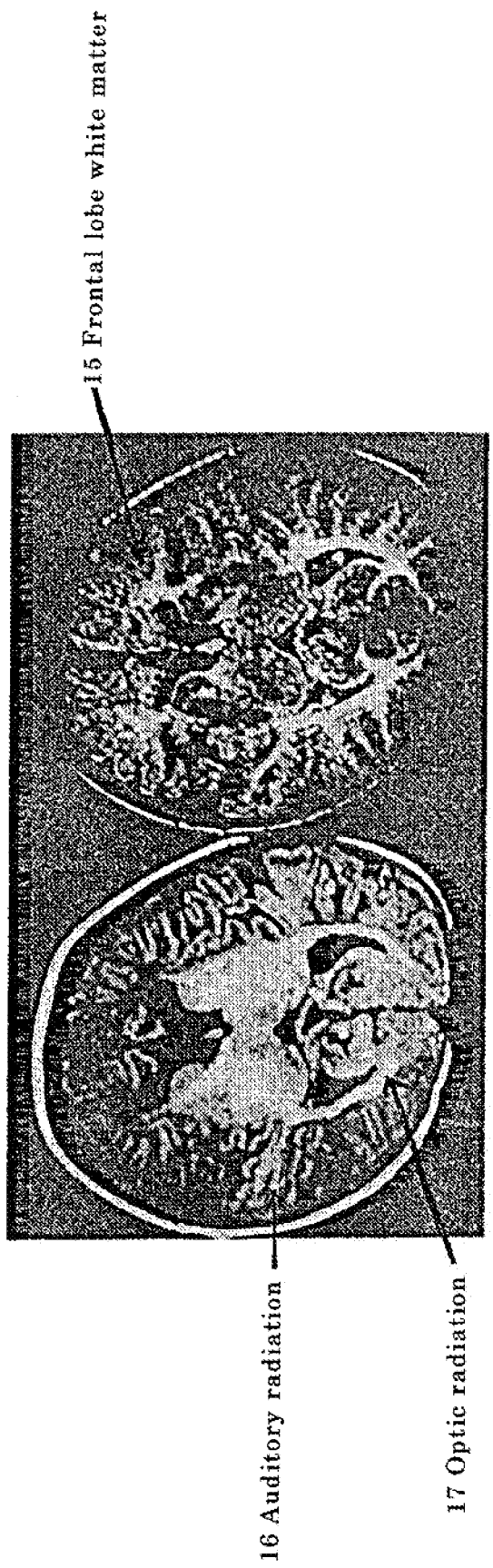
FIG. 32 are explanatory views: (A) shows a FLAIR image (TE=20 ms) of white matter branching; (B) shows a FLAIR image (TE=180 ms) predicting branching growth.

FIG. 32 is explanatory views: (A) shows a FLAIR image (TE=20 ms) of white matter branching, and (B) shows a FLAIR image (TE=180 ms) predicting branching growth. From FIG. 32, it can be seen that by obtaining FLAIR images with short TE and long TE while keeping the other conditions the same, white matter in the area around the frontal lobe white matter 15, auditory radiation 16 and optic radiation 17, which did not stand out in the white matter branching image, shows very clearly as white in the branching growth prediction image.

Figure 33:
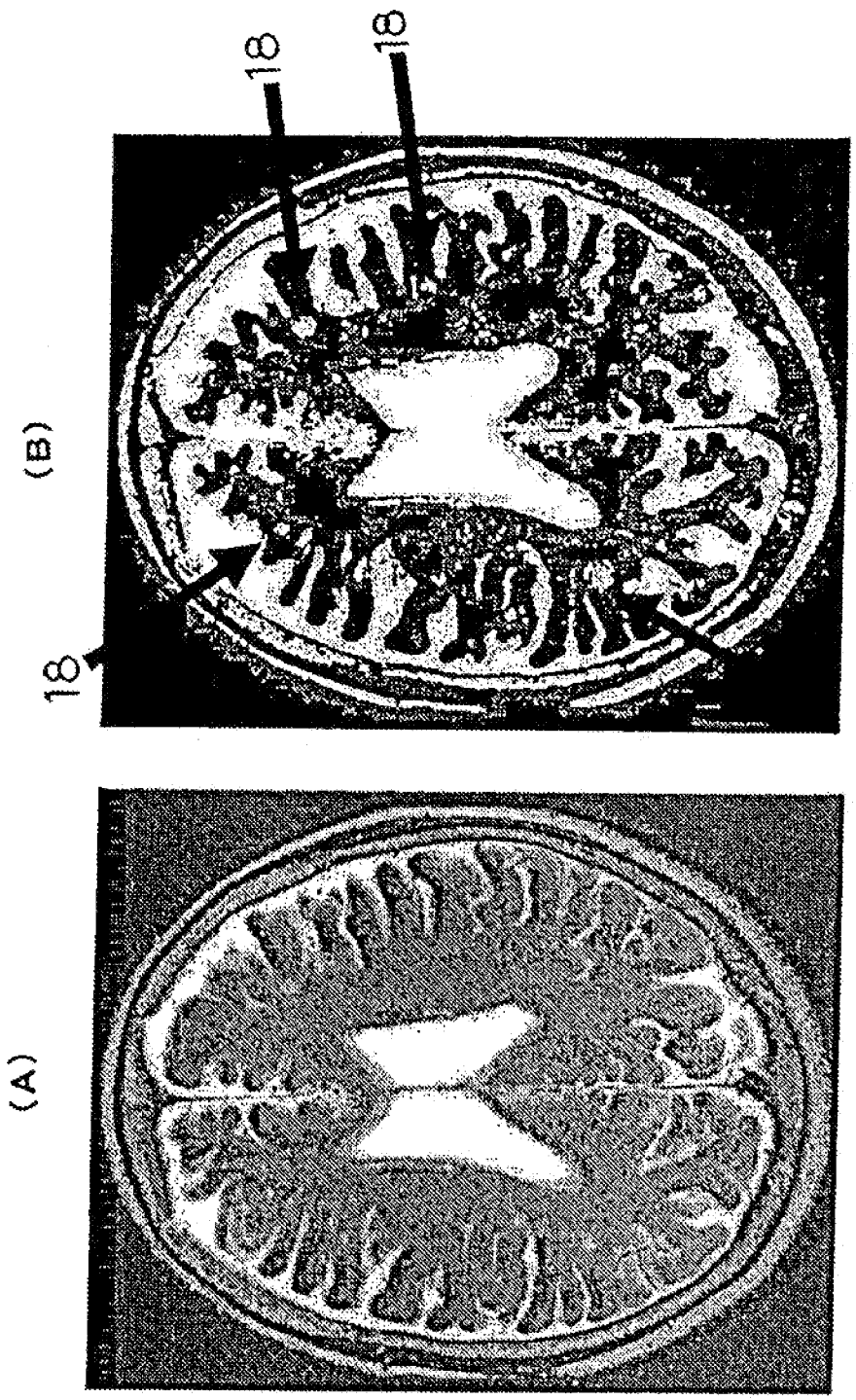
FIG. 33 are explanatory views: (A) shows a T2-weighted image; (B), a brain branching image.

FIG. 33 is explanatory views: (A) shows a T2-weighted image, and (B), a brain branching image. As shown by the arrows in FIG. 33, the image of small moth-holes in the branches, namely, lacunar infarcts in the cerebral white matter 18 are found to be clearly displayed.

Effect of the Invention

The embodiment of the present invention displays excellent effects, such as the following:

Effect 1. The thickness of the cortex is 2-3 mm, and it is difficult to differentiate its distinguishing characteristics from growth, atrophy and the like, from brain address to brain address; but by viewing the shape of the white matter, variations in change are enhanced and they can be compared by brain address.

Effect 2. The brain is said to comprise 13 billion neurons, but while on the one hand, the number of neural cells decreases after birth, it has been pointed out that the amount of white matter in the entire brain increases up to around age 50; and thus displaying branching makes it possible to evaluate growth, brain address by brain address.

Effect 3. The fact that branching of the white matter under the cortex is taken as the target of imaging makes it possible to see the development of branches, which reflect the development of the cortex. The state of network activity cannot actually be seen from images of the cortex.

Effect 4. It is possible to quantify branching and the shape of brain white matter branches (number, thickness, growth, etc. of branches).

Effect 5. Differences in white matter branching, which were formerly difficult to distinguish in brain pathology, can be differentiated by color.

Effect 6. The strongest brain addresses and lowest brain addresses can be distinguished and extracted from branching that is color-coded. The difference between developed brain addresses and weakened brain addresses can be seen visually.

Effect 7. Left/right branching ratios can be compared quantitatively (in 2 and 3 dimensions).

Effect 8. The contrast ratio W/C=E between the cortex (C) and the white matter (W) is adjusted by changing the window width (WW) and the window level (WL). By varying the contrast ratio E to draw a color-coded contour image, branch surface area and volume ratios can be calculated, not only for the whole brain, but also for arbitrarily selected brain addresses.

Effect 9. Branching characteristics, such as the strongest addresses and left/right differences, can be quickly extracted from contour images. They can be displayed as maps to brain addresses, contour maps with brain addresses, and so on.

Effect 10. By this means, rates of branch growth for brain addresses are displayed and quantified.

Effect 11. Because the white matter can be clearly differentiated without looking at the cortex, the shape of the white matter can be grasped at a glance.

Effect 12. Individual brain characteristics can be subdivided (in the same way as for blood types) and differentiated for healthy individuals who are not ill. Namely, group analysis of the shape of the white matter, not the cortex, can be performed, and individual brain characteristics can be defined.

Effect 13. Because it becomes possible to differentiate distinguishing characteristics of brain addresses on an individual level, whether it is a question of branches that are left or right dominant in the frontal lobe, or branches that are left or right dominant in the posterior temporal lobes, or in the parietal lobe, it can be "diagnosed" which branches or which brain addresses an individual has developed in his or her life, even after entering adulthood.

Effect 14. Two staining with myelin basic protein (MBP) and the phospholipids of Luxol fast blue (LFB) show substantial discrepancies in white matter development. This, however, could not be differentiated with brain branching in brain MRI. By changing the echo time settings in FLAIR for classifying myelin stages, images predicting future myelin growth and images predicting future brain branching can be created.

Effect 15. By comparing behavior and brain address function, it is possible to discover which brain addresses are currently developing.

Effect 16. When this brain branching imaging method is used, it is not only possible to determine the brain addresses where white matter myelination has taken place, but, in the same way that trunks and branches of trees differ in thickness, density and character, stages in growth of the white matter can also be distinguished. In particular, it is possible to distinguish strong branches where myelination is already finished and branches showing indications of future development.

Effect 17. Clear vectors of hidden brain branching growth can be drawn.

After 30 weeks gestation, brain branching growth begins to occur actively. This is around 2 months before a child is born and enters the world outside. When brain branching growth occurs, the branches run unrestrainedly within the confines of the brain.

When, however, this growth process is observed with MRI and followed closely over the years, different things become apparent from when this narrow world was observed with a microscope.

One difference is vectors of branching growth that advance in 3 directions inside the brain. In order for the brain to grow, it is necessary for information to be carried to the brain from the senses—sight, hearing, etc. And among the senses, the brain addresses related to touch, hearing and sight are located divided in 3 directions, much like Fleming's rule.

Figure 34:
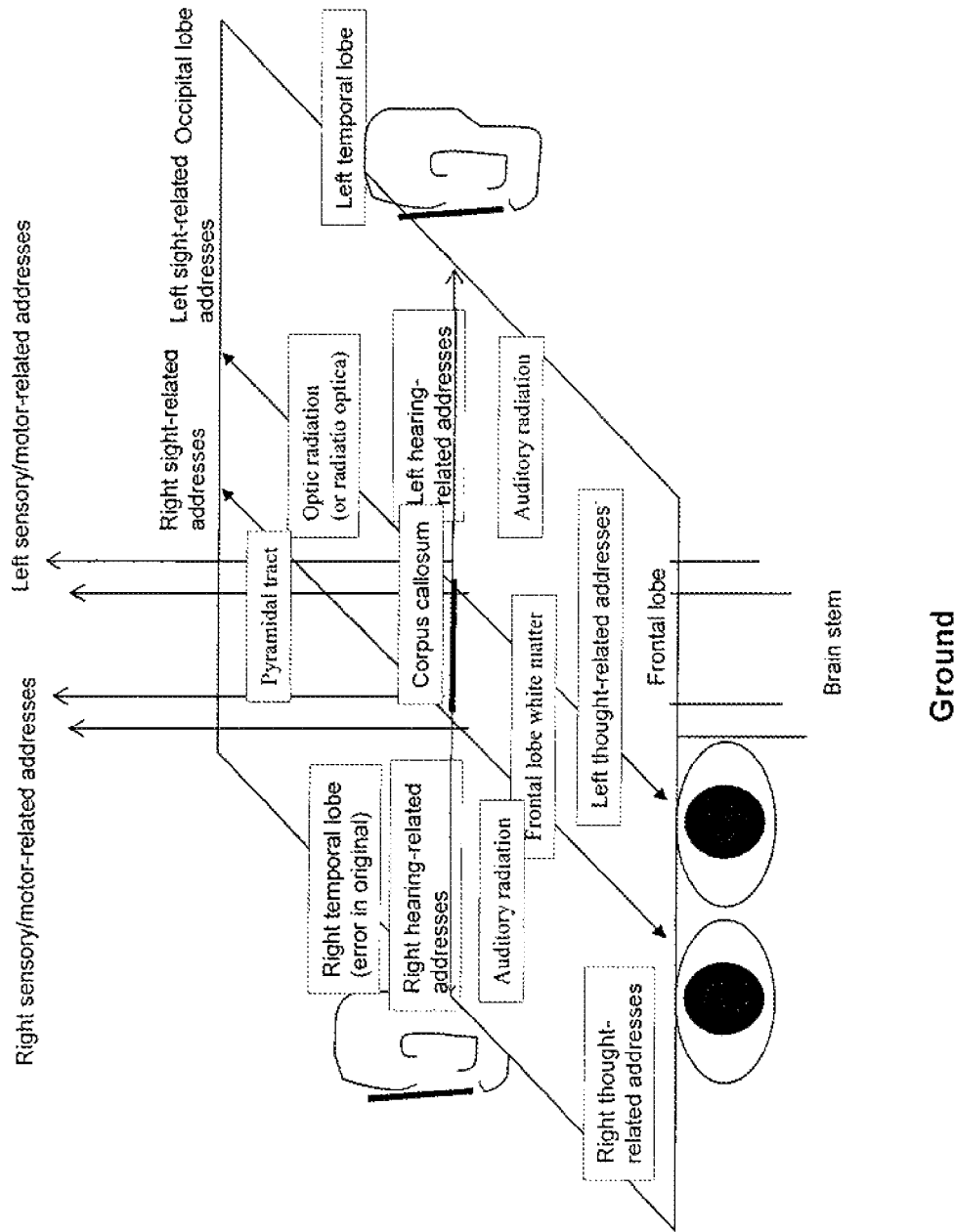
FIG. 34 is an explanatory view that shows brain branching growth vectors.

FIG. 34 is an explanatory view showing brain branching growth vectors.

As shown in FIG. 34, if you feel the occipital area from outside the scalp, there is a protruding part known as the occipital protuberance in the occipital lobe. Inside this protruding part are the sight-related brain addresses, the location of "seeing".

Sight-related addresses are located perpendicular to the hearing-related brain addresses, which are right near the right and left ears, in a horizontal plane.

The sensory-related brain address 3, which is involved in the sense of touch, such as skin touch, and motor-related brain address 4, which moves the body, are located parallel to each other, as if drawn in arcs from the left and right ears. Although the motor-related brain address is not included in the senses, it is contiguous with the sensory-related brain address and grows together with it. This locational relationship suggests that not only the senses, but also the ability to move the body are essential to building the foundation of brain growth.

In this way, branches growing from the deep regions of the brain, such as the thalamus, are built up solidly from around birth through infancy towards the motor/sensory-related addresses, vision-related addresses and hearing-related addresses.

That is, the sight-related addresses spread their branches from the optic radiation, the hearing-related addresses spread their branches from the auditory radiation, and the motor/sensory-related addresses spread their branches from the pyramidal tract.

Thought-related addresses develop intricately as the frontal lobe white matter spreads its branches.

As can be seen in FIG. 34, by taking the optic radiation, auditory radiation, pyramidal tract and frontal lobe white matter as standards for their respective vectors of brain branching growth, branching can be displayed in such a way that it is possible to determine which of the brain addresses— vision-related, hearing-related, motor/sensory-related or thought-related—is growing dominantly, also including left/right dominance for those branches.

That is, it is possible to extract the characteristics of each of these systems even within the entire brain, and view the individuality of the brain from its branching.

The present invention is not limited to the aforementioned embodiments, but may be carried out in any of various other forms without departing from the sprit and scope of the invention as defined in the claims.

INDUSTRIAL APPLICABILITY

Because the present invention creates white-matter-enhanced images in which the brain white matter is enhanced from contrast images of the brain of a living body obtained from an MRI apparatus, it can be used for analyzing distinguishing characteristics of the brain of a living body, such as degree of growth and development, left/right brain dominance, identification of areas of strength and weakness, group analysis of white matter growth types, and personality traits of the brain of the living body.

The invention claimed is:
1. A white-matter-enhancement apparatus comprising:
a white-matter-enhanced image-creating computer processor that creates a white-matter-enhanced image based on a contrast image of a brain of a living body received from a magnetic resonance imaging (MRI) apparatus, wherein white matter is enhanced by adjusting the contrast image in such a way that the white matter stands out, a cortex does not stand out, and branches of the white matter are visible;

a display device that displays the white-matter-enhanced image; and a branching analysis computer processor that quantitatively measures at least an intensity of selected demarcating regions of the branches of the white matter in the white-matter-enhanced image and analyzes distinguishing characteristics of the brain, based on at least the intensity of the selected demarcating regions, wherein the selected demarcating regions are assigned as regions where specified functions and roles are performed in the brain of the living body;

wherein the branching analysis computer processor quantitatively measures the intensity of the selected demarcating regions by counting one of a first number of black voxels and a second number of white voxels in the selected demarcating regions in a left brain and a right brain and analyzes at least left/right brain dominance as a distinguishing characteristic by calculating a Laterality Index LI according to a formula $$LI=(R-L)/(R+L),$$

wherein L=the first number of black voxels or the second number of white voxels counted in the selected demarcating regions in the left brain, and R=the first number of black voxels or the second number of white voxels counted in the selected demarcating regions in the right brain, and wherein if LI is negative, left brain dominance is strong for the selected demarcating regions, and if LI is positive, right brain dominance is strong for the selected demarcating regions.

2. The white-matter-enhancement apparatus of claim 1, wherein the contrast image is a T1-weighted image, a proton density-weighted image, a T2-weighted image, a FLAIR (Fluid Attenuated Inversion Recovery) image or a diffusion-weighted image, or an image that is a combination thereof.

3. The white-matter-enhancement apparatus of claim 1, wherein the white-matter-enhanced image is created by adjusting a window width and a window level.

4. The white-matter-enhancement apparatus of claim 1, wherein addresses for demarcating regions of the brain are displayed together with the white-matter-enhanced image.

5. The white-matter-enhancement apparatus of claim 1, wherein the branching analysis computer processor further creates and analyzes a plurality of types of classifications based on measurements of at least intensities of the selected demarcating regions of white-matter-enhanced images of brains of living bodies.

6. The white-matter-enhancement apparatus of claim 1, wherein the distinguishing characteristics include a degree of growth and development, left/right brain dominance, an identification of areas of strength and weakness, and personality traits.

7. The white-matter-enhancement apparatus of claim 1, wherein the selected demarcating regions are brain addresses.

8. The white-matter-enhancement apparatus of claim 1, wherein the branching analysis computer processor further quantitatively measures at least one of a number, a thickness, a length, or a size of the branches of the selected demarcating regions of the branches of the white matter in the white-matter-enhanced image and analyzes the distinguishing characteristics of the brain, based on at least one of the number, the thickness, the length, or the size.

9. The white-matter-enhancement apparatus of claim 1, wherein the selected demarcating regions are in the left brain and the right brain.

10. The white-matter-enhancement apparatus of claim 1, wherein the branching analysis computer processor further analyzes a shape of the branches of the selected demarcating regions of the branches of the white matter in the white-matter-enhanced image and analyzes the distinguishing characteristics of the brain, based on the shape.

11. A method of white-matter-enhancement, using a computer including a display device and a controller, wherein the controller is communicatively coupled to an MRI apparatus and has a non-transitory memory device that receives and stores contrast images obtained by the MRI apparatus, the method comprising:

storing in the non-transitory memory device a contrast image of a brain of a living body received from the MRI apparatus;

creating a white-matter-enhanced image using the controller, based on the contrast image stored in the non-transitory memory device, in which the white matter is enhanced by the controller by adjusting the contrast image in such a way that the white matter stands out, a cortex does not stand out, and branches of the white matter are visible;

displaying the white-matter-enhanced image created using the controller; and quantitatively measuring at least an intensity of selected demarcating regions of the branches of the white matter in the white-matter-enhanced image; and analyzing distinguishing characteristics of the brain, based on at least the intensity of the selected demarcating regions, wherein the selected demarcating regions are assigned as regions where specified functions and roles are performed in the brain of the living body, wherein the quantitatively measuring at least the intensity of the selected demarcating regions further comprises quantitatively measuring the intensity of the selected demarcating regions by counting one of a first number of black voxels and a second number of white voxels in the selected demarcating regions in a left brain and a right brain and the analyzing the distinguishing characteristics of the brain further comprises analyzing at least left/right brain dominance as a distinguishing characteristic by calculating a Laterality Index LI according to a formula $$LI=(R-L)/(R+L),$$

wherein L=the first number of black voxels or the second number of white voxels counted in the selected demarcating regions in the left brain, and R=the first number of black voxels or the second number of white voxels counted in the selected demarcating regions in the right brain, and wherein if LI is negative, left brain dominance is strong for the selected demarcating regions, and if LI is positive, right brain dominance is strong for the selected demarcating regions.

12. The method of white-matter-enhancement of claim 11, further comprising quantitatively measuring at least one of a number, a thickness, a length, or a size of the branches of the selected demarcating regions of the branches of the white matter in the white-matter-enhanced image and analyzing the distinguishing characteristics of the brain, based on at least one of the number, the thickness, the length, or the size.

13. The method of white-matter-enhancement of claim 11, wherein the selected demarcating regions are in the left brain and the right brain.

14. The method of white-matter-enhancement of claim 11, further comprising analyzing a shape of the branches of the selected demarcating regions of the branches of the white matter in the white-matter-enhanced image and analyzing the distinguishing characteristics of the brain, based on the shape.

\* \* \* \* \*